US012778424B2

(12) United States Patent
Rivlin et al.

(10) Patent No.: US 12,778,424 B2
(45) Date of Patent: Nov. 3, 2026

(54) APPARATUS FOR ANATOMIC THREE DIMENSIONAL SCANNING AND AUTOMATED THREE DIMENSIONAL CAST AND SPLINT DESIGN

(71) Applicant: Dimension Ortho Inc., Philadelphia, PA (US)

(72) Inventors: Michael Rivlin, Philadelphia, PA (US); Ashkan Sedigh, Philadelphia, PA (US); Amir Reza Kachooei, Philadelphia, PA (US); Michael J. Sileski, Philadelphia, PA (US); Alexander R. Vaccaro, Philadelphia, PA (US); Pedro K. Beredjiklian, Philadelphia, PA (US)

(73) Assignee: DIMENSION ORTHO INC., Philadelphia, PA (US)

( * ) Notice: Subject to any disclaimer, the term of this patent is extended or adjusted under 35 U.S.C. 154(b) by 38 days.

(21) Appl. No.: 19/045,678

(22) Filed: Feb. 5, 2025

(65) Prior Publication Data

US 2025/0176832 A1 Jun. 5, 2025

Related U.S. Application Data

(63) Continuation of application No. 17/914,948, filed as application No. PCT/US2021/024756 on Mar. 30, 2021, now Pat. No. 12,239,411.

(Continued)

(51) Int. Cl.

| | |
|---|---|
| ***A61B 5/00*** | (2006.01) |
| ***G06T 3/40*** | (2006.01) |

(Continued)

(52) U.S. Cl.

CPC .......... *A61B 5/0064* (2013.01); *A61B 5/0077* (2013.01); *G06T 3/40* (2013.01);

(Continued)

(58) Field of Classification Search

CPC .. A61B 5/0064; A61B 5/0077; H04N 13/243; H04N 13/282; G06T 3/40; G06T 17/00

(Continued)

(56) References Cited

U.S. PATENT DOCUMENTS

| | | | | |
|---|---|---|---|---|
| 5,870,220 A * | 2/1999 | Migdal | ................. | G02B 26/12 250/559.22 |
| 10,758,396 B2 | 9/2020 | Rivlin et al. | | |

(Continued)

FOREIGN PATENT DOCUMENTS

| | | |
|---|---|---|
| CN | 104266587 B | 4/2017 |
| DE | 102011119658 B4 | 4/2014 |

OTHER PUBLICATIONS

Chris Welch, 3D-printed 'Cortex' cast concept puts a modern spin on bone fracture treatment, The Verge, Jun. 29, 2013.

(Continued)

*Primary Examiner* — Matthew David Kim

(74) *Attorney, Agent, or Firm* — Panitch Schwarze Belisario & Nadel LLP

(57) ABSTRACT

A scanner system for capturing a three-dimensional model of an object includes a laser and a camera to capture two-dimensional images of the object. The system also includes a tube mounted to a rail, a central processor configured to receive data collected from the laser and the camera and an actuation mechanism configured to move the tube along the rail. The tube is configured to move generally along a travel axis of the rail. The tube includes open first and second tube ends. The laser and camera are mounted inside the tube between the first and second tube ends. The first tube end includes a first continuous ring and the second tube end includes a second continuous ring. A channel extends through the tube between the first and second rings positioned adjacent the rail in an assembled configuration.

44 Claims, 12 Drawing Sheets

Related U.S. Application Data

(60) Provisional application No. 63/077,189, filed on Sep. 11, 2020, provisional application No. 63/016,492, filed on Apr. 28, 2020, provisional application No. 63/001,945, filed on Mar. 30, 2020.

(51) Int. Cl.

| | |
|---|---|
| ***G06T 17/00*** | (2006.01) |
| ***H04N 13/243*** | (2018.01) |
| ***H04N 13/282*** | (2018.01) |
| *A61B 34/10* | (2016.01) |

(52) U.S. Cl.
CPC ........... *G06T 17/00* (2013.01); *H04N 13/243* (2018.05); *H04N 13/282* (2018.05); *A61B 2034/105* (2016.02)

(58) Field of Classification Search
USPC ........................................................... 348/48
See application file for complete search history.

(56) References Cited

U.S. PATENT DOCUMENTS

| | | | | |
|---|---|---|---|---|
| 12,521,016 | B1 * | 1/2026 | Epstein | A61B 5/0064 |
| 2010/0087803 | A1 | 4/2010 | Rastegar et al. | |
| 2010/0138193 | A1 * | 6/2010 | Summit | A61F 5/022 703/1 |
| 2016/0339230 | A1 * | 11/2016 | Muñoz | A61N 1/36071 |
| 2016/0374431 | A1 * | 12/2016 | Tow | A43D 1/022 36/43 |
| 2017/0104925 | A1 * | 4/2017 | Ng | A61B 5/445 |
| 2017/0360578 | A1 * | 12/2017 | Shin | G09B 23/286 |
| 2018/0028108 | A1 * | 2/2018 | Shluzas | A61B 5/445 |
| 2018/0144547 | A1 * | 5/2018 | Shakib | G06T 15/503 |
| 2018/0321374 | A1 * | 11/2018 | Qi | G01S 13/887 |
| 2020/0238626 | A1 * | 7/2020 | Bleicher | A43D 1/025 |
| 2020/0275862 | A1 * | 9/2020 | Fennell | A61F 5/01 |
| 2021/0000617 | A1 * | 1/2021 | Gao | G06T 7/0014 |

OTHER PUBLICATIONS

Icon Magazine, 2013 Icon Awards winner—Cortex 3D-printed cast, Technology of the Year, Jan. 23, 2014.
Stoppress Team, New Zealander's 3D printed design could do away with smelly casts forever, Jul. 9, 2013.
Randall Marsh, 3D-printed Cortex concept scratches the itch of healing broken bones, Jul. 2, 2013.
Nina Golgowski, Revolutionary 3-D printed cast could be the future of comfort and design—New York Daily News, Jul. 14, 2013.
Rose Etherington, Cortex 3D-printed cast for fractured bones by Jake Evill, DeZeen, Jun. 28, 2013.
Jake Evill, CORTEX—Exoskeleton Protecting the Internal Skeleton, 2013.
Deniz Karasashin, Osteoid Medical Cast, attachable bond stimulator, A'Design Award & Competition, Mar. 23, 2014.
Extended European Search Report in European Patent Application No. 21782287.3 dated Apr. 4, 2024.

* cited by examiner

APPARATUS FOR ANATOMIC THREE DIMENSIONAL SCANNING AND AUTOMATED THREE DIMENSIONAL CAST AND SPLINT DESIGN

CROSS-REFERENCE TO RELATED APPLICATIONS

The present application is a continuation of U.S. patent application Ser. No. 17/914,948, filed Sep. 27, 2022 and titled, "Apparatus for Anatomic Three-Dimensional Scanning and Automated Three-Dimensional Cast and Splint Design," which is a Section 371 of International Patent Application PCT/US21/24756, filed Mar. 30, 2021, and titled, "Apparatus for Anatomic Three-Dimensional Scanning and Automated Three-Dimensional Cast and Splint Design," and claims the benefit of U.S. Provisional Patent Application Nos. 63/077,189, filed Sep. 11, 2020 and titled, "Apparatus for Anatomic Three Dimensional Scanning and Automated Three Dimensional Cast and Splint Design;" 63/001,945, filed on Mar. 30, 2020 and titled "Apparatus for Anatomic Three Dimensional Scanning and Automated Three Dimensional Cast and Splint Design" and 63/016,492, filed Apr. 28, 2020 and titled "Apparatus for Anatomic Three Dimensional Scanning and Automated Three Dimensional Cast and Splint Design" the entire contents of which are incorporated herein by reference in their entirety.

BACKGROUND OF THE INVENTION

Three-dimensional ("3D") scanners are widely used in different industries such as additive and subtractive manufacturing, aerospace, automotive, consumer goods, industrial goods, orthodontics, orthopedics and related sectors and industries. In addition, three-dimensional scanners are commonly used in Augmented Reality ("AR") and Virtual Reality ("VR") devices. Each application requires certain features and qualities in the 3D model that is developed. For example, in orthopedics and orthodontics, accuracy and precision are important parameters for the medical specialists. In AR and VR, the color data (red, green, blue ("RGB") point cloud) of the model is often more important than other factors.

A patient's arm or foot is immobilized by circulating roles of plaster, resin or fiberglass around the impacted anatomy when casting the patient's injured arm, foot, leg or other body part. Although it can be applied in a very short time, there are shortcomings with prior art casting and methods. Conventional casts are not resistant to water and lose their properties over time, which can have a negative impact on patient outcomes. The conventional plaster casts severely limit activity of the patient by requiring avoidance of water, limiting sweating and otherwise avoiding any activity that could introduce foreign substances into the space between the cast and the patient's skin. Another problem is that there is no lattice or holes in the cast to let air flow though the cast to avoid or limit sweating and subsequently avoid or limit skin itching, as well as to monitor and treat the patient's skin. The lack of lattice or holes also prevents foreign substances from being removed from the patient's skin and can cause severe irritation by rubbing against the patient's skin. The patient's skin may require or benefit from treatment as the result of the event causing the patient's injury or as a result of foreign object irritation while wearing the cast. In the conventional casting system and process, the patient has to keep his or her arm or foot still for a long time before the cast dries and hardens, whereas the scanning process may be completed in shorter amounts of time.

Laser scanners may be constructed or adapted for portability or may be constructed or adapted for hand-held use. The laser scanner may be coupled to a robotic arm or Articulated Arms Coordinate Measuring Machines (AACMM) for automated processing. For these scanners, the operator or the robotic arm turns or moves the object around to capture all or most of the points on the surface of the object. In these rotating 3D scanners, the process of capturing all or most points for the hand or foot takes between one to five minutes (1-5 min), which is a significant period of time for a typical patient to hold the arm, foot or other body part in a generally immobile position without movement. There are other methods of 3D scanning such as photogrammetry in which ten to twenty (10-20) digital single-lens reflex ("DSLR") cameras are set at fixed positions around the object to capture two-dimensional ("2D") images and the 2D images are merged into a 3D point cloud or to facilitate development of a 3D model. Although this method is relatively quick during processing, it is not a cost-effective process for medical applications. This particular system and method also require a designated space for the set-up, which may not be possible in all medical facilities. There is another type of photogrammetric 3D-scanning in which one camera is turned around the object to provide twenty to forty (20-40) photos of the object. This method is cost-effective but lacks speed, accuracy, precision and is mostly used for in-home applications. The preferred 3D scanner and related methods address the shortcomings of the prior art devices and methods to provide an accurate scan of a patient's anatomy, transform the scan into a 3D model and define a cast or splint based on the 3D model.

BRIEF SUMMARY OF THE INVENTION

Briefly stated, the preferred apparatus for anatomic three-dimensional ("3D") scanning and automated three dimensional cast and splint design may be comprised of any capturing device that can be used as a capturing system, preferably for capturing a 3D image of a patient's anatomy. The camera is used as a general word in this description that will not be limited specifically to the camera devices, but may also encompass scanners, probes, x-ray imagers and related systems that are able to acquire data to develop a 3D image or model preferably of the patient's anatomy. Any similar names to this such as webcam, imager, scanner and related features are possible to be used for operation of the preferred system. The number of cameras may vary in this process based on the complexity of the object geometry input.

The process of casting an injured body limb may comprise 3D scanning, 3D model creation, designing process, 3D printing, and post-printing processing.

The preferred 3D scanner machine relates generally to a scanning apparatus that emits laser beams on the object and captures the reflections by a number or array of cameras. The lasers and the cameras move on a linear track relative to a patient's anatomy to cover different parts of the object or to develop the 3D model, preferably of the patient's anatomy that the physician is treating. During this scanning or imaging process, the camera(s) preferably captures the two-dimensional ("2D") images of the object and sends the raw image data to the computer, controller or central server. The images may also be otherwise captured, such as by stereoscopic imaging techniques or stereoscopic photography. The software of the computer, controller or central server processes the captures or acquired images and constructs the three-dimensional digital file of the object, preferably the impacted or injured portion of the patient's anatomy.

Physicians, providers, and techs use the 3D digital file, preferably a model of the hand, arm, foot, torso, hips, shoulder and other parts of the limbs or body of the patient, to design and 3D-print custom-made cast, splint, orthopedic brace, and related medical device. The process of designing is performed by creating a surface over the 3-D scanned part which is used to design the cast, splint, brace or other medical device for patient treatment. Moreover, this process includes merging other elements such as locks, lattice engraving, attachments such as smart devices/microchips/sensors, access ports, stimulation ports or any identity documents for printing on the surface of the medical device and related features.

An accurate and a high precision resolution output model is preferred in orthopedics. In addition to accurate and high precision, the process of capturing images should be as quick as possible to avoid anomalies or errors resulting from the patients' arm, foot or other anatomy moving or shaking during scanning. It is also more convenient for the patient to be scanned in the shortest possible time which enhances the ability to produce an accurate scan as the body remains immobile during scanning.

Scanning and adaptable casting, as is described herein makes it possible for the patient to wear the cast, brace, splint and etc. on his/her own. The preferred lattice and locks on the computer-based and designed casts or splints alongside with resistance of the 3D printing materials to water and other potential contaminants, make the 3D printed casts and splints a better alternative to traditional casting, especially for patients that require a longer time of immobilization or temporary immobilization over predefined time periods over a long timeframe, such as wearing the case, brace or splint only at night.

In another aspect, the preferred invention is directed to a scanner system for capturing and making a 3D digital file of an object. The captured object can be any object fitting inside the area of the scanner, such as an arm, leg, foot, joint, torso, shoulder or other anatomical feature of a patient. The preferred scanner system is able to scan the healthy or injured body limbs or other object and develop a 3D model of the scanned object or anatomy. However, the preferred system and method of this 3D scanning system is not limited to the embodiments and methods described herein but is able to take on variations that would be apparent to one having ordinary skill in the art based on a review of the present disclosure.

The three-dimensional scanner of the preferred embodiments is designed to capture points on the surface of an object with a high precision and fast operation, preferably less than ten seconds (10 s). This preferred apparatus uses at least one laser beam as a projector and reflecting mirrors to cover the bottom, top, left and right side of the object. Three laser beams, for example, may illuminate the different slices of the object and preferably at least four Complementary Metal Oxide Semiconductor ("CMOS") cameras close to the lasers capture the reflected points from the object. The preferred embodiments of the present invention are not limited to inclusion of the three laser beams and the four CMOS cameras for operation and may utilize alternative imaging and sensing systems, mechanisms and methods for capturing the data for creation or development of the 3D model.

The preferred scanning machine includes three (3) main cameras. Backup cameras, however, may be used to cover blind spots of the preferred main cameras in complex geometries or for capture of additional details of the object. The backup cameras are preferably active in situations where the main cameras miss or could potentially miss a blind spot on the object and the central processor may direct the main and backup cameras to take images, based on initial images from the main cameras, input from a technician or user or based on other factors related to the object or the particular scanning situation. If the central processor or technician determines that the initial scan does not capture portions of the object or there is a potential blind spot, the backup camera preferably verifies the same coordinates to complete the point cloud of the object. This process preferably eliminates the need to repeat the scanning when there are backup cameras, because the backup cameras are able to address potential blind spots or limits to resolution of the object. The raw image data acquired from the cameras are preferably sent to the central processor for further processing in the 3D-scanner customized software. After analyzing the raw 2D images, the preferred software converts those images to the point cloud and constructs the 3D digital file in the preferred format for the user. It is then possible to use the end model to design custom-made casts, splints, braces, medical devices and similar orthoses or prostheses with this software automatically or manually, engraving shapes, locking mechanism insertions and related features on the casts and/or splints.

The preferred 3D scanning mechanism can generate an orthopedic cast, brace, and splint (orthoses) with the included software in an automated or manual method based on the input features, such as wounds, deformities, irregularities and related features of the object, also with 2D images based on the extracted features. Soft computing techniques are utilized in offline and online methods to generate custom-made casts with inserted lock, size, lattice and patients' desirable shapes and textures, as well as potentially additional features. Appendicular and built-in parts (such as sensors, clasp, locks, etc.) are also placed through the user interface or by artificial intelligence ("A.I.") algorithms or computation methods. The preferred system also predicts the mechanical properties and optimizes the 3D-printing parameters in the cast design under the pre-defined constraints. Augmented reality is preferably utilized in the process to automatically visualize and guide the customer, technician or user.

The preferred invention is directed to a virtual fitting of prefabricated orthoses, such as braces, splints, neck collars, boots, knee immobilizers and related prefabricated splints, braces and casts. The orthoses may be designed and developed by third parties or may be designed and developed by the manufacturer or designer of the preferred apparatus for anatomic three-dimensional scanning and automated three-dimensional casts and splints.

In another aspect, the preferred invention is directed to a method of processing and making a custom splint, cast, braces or other orthopedic support based on a pre-printed model, such as a hand model, or pre-printed base orthotic model. A Machine learning algorithm finds the closest 3D base model of the pre-printed base models with classification and parameter estimation. An application on a mobile device or a website page runs a process for capturing images/videos of the patient's body part and generating 2D models with estimated parameters for the virtual 3D model that is utilized to select the appropriate base model from the inventory of base models. The process then utilizes any material that is used in making casts, braces, or splints through cutting, machining or otherwise using additive or subtractive manufacturing techniques to obtain the proper shape for the specific patient's body part. The template or selected base model is then shaped on the generated patient model or inventory model template to produce a final cast or splint for application to the patient's body part. Post-production shaping and modification may be automated by heating the model or other means of affecting the properties of the orthoses, such as 3D printing, machining or otherwise manipulating the 3D base model to define the final cast or splint.

In another aspect, the preferred invention is directed to a scanner system for capturing a three-dimensional model of an object, preferably a body part of a patient, including lasers providing a stripe of light to illuminate the object, capturing devices to capture 2D images of the object, a central processor configured to receive data collected from the lasers and capturing devices and send commands and data, an actuation mechanism including a motor and encoders configured to move the capturing devices and the lasers, a graphical user interface to process the 2D images and construct a 3D model, and a nozzle that builds the generated 3D model in a scanner chamber which has a heat-bed on a scanning plane. The scanner system also includes mechanical elements, including a belt, ball bearings, a roller bearing, position sensors and a coupling component to attach the belt to moving planes and three planes to fix the cameras and lasers while moving on a track. The capturing devices include cameras. The graphical user interface is configured to navigate over a 3D model of the object. The scanner system utilizes 3D-printing parameters optimization, mechanical properties prediction, mesh post-processing, and the data for orthopedic applications such as designing cast, splint, braces and orthoses.

In a preferred scanner system, the cameras are configured to capture main points of the object. The cameras include a backup camera and main cameras. The backup camera is configured to cover blind spots of the object hidden from the main cameras. The nozzle of the preferred system is configured to construct the 3D model with photogrammetry techniques based on the images captured by the cameras. The central processor of the system preferably detects missing points of the data related to the object and actuates a backup camera of the cameras to automatically perform a task, such as collecting data related to a hidden area of the object. The number of cameras utilized in the preferred system is not limiting and the number of cameras can be decreased or increased without significantly impacting the performance of the scanner system in appropriate design circumstances. The lasers and cameras are preferably configured to scan a side of the object with a main camera of the cameras and a backup camera. The preferred central processor is configured to conduct post-processing including an outer base design such as a cast, a splint, a brace, lock insertions, a mesh inspection and basic operators. The central processor is preferably configured to attain a faster scanning operation utilizing an additional main camera and a backup camera. The number of lasers utilized in the preferred system is not limiting and the number of lasers can be decreased or increased. The preferred lasers and cameras are configured to scan a side of the object utilizing a first laser of the lasers. The lasers preferably include additional lasers to switch the scanner system into a multi-laser operation mode. The central processor is configured in the preferred embodiments to acquire valid models of the object with possible movement or shake of the object during scanning by decreasing a scanning period to five (5) seconds or a reasonable time period that limits model errors resulting from movement of the object during scanning. The preferred scanner may alternatively include post-processing software corrections designed to account for movement or shaking of the object during scanning. The scanner system of the preferred embodiments further includes an automated uniform-making process to reconstruct incomplete surfaces of the object during scanning by utilizing a main camera and a backup camera of the cameras.

The scanner system of the preferred embodiments may include a rate of photo capturing of the cameras, wherein the rate of photo capturing is approximately eighty (80) frames per second. The rate of photo capturing of the preferred scanner system facilitates capture with a step-size of approximately one millimeter for the object. A speed of scanning of the scanner system can preferably be increased based on the actuation mechanism speed. A scanning size of the preferred scanner system can be varied based on a size of the scanner chamber.

The preferred central processor includes an algorithm that reconstructs orthopedic casts, splints, and braces automatically based on a prescribed size, application, features such as deformities, ulcers, sores, wounds, and related features automatically or manually. The preferred algorithm of the scanner system is utilized to optimize 3D-printing parameters such as infill percent, lattice shape, shell size, speed, raster angle, orientation, and related features based on desired mechanical output properties including shear, compressive strength, flexural strength, surface roughness, and 3D-printing time-cost model. The scanner system of the preferred embodiments may also include a machine that is trained with soft computing techniques to predict mechanical properties of the 3D model including shear, compressive strength and flexural strength. The algorithm of the preferred embodiments in the central processor predicts a size of the object based on previously trained data with features of limbs, body parts, age, sex, and any curves in the object. The algorithm also preferably generates a 3D file of an orthopedic cast, splint, or brace based on predicted features of the object, wherein the object is comprised of a hand or other body part of the patient and the predicted featured is based on hybrid soft computing techniques. The preferred algorithm is comprised of a learning algorithm to classify input object features including wounds, deformities, sores, and related features to reconstruct the 3D model. The 3D model produced from the preferred algorithm is comprised of an orthopedic cast, brace or splint. The preferred algorithm is configured to locate electric pads or medical transducers in the 3D model based on predicted features. The algorithm is comprised of a preferred decision-making algorithm to decide final 3D-printing parameter sets in a Pareto-front optimal solution with many-objective optimization. The algorithm preferably includes online or offline learning methods to fit complex curves automatically on the 3D model based on unseen or trained features of a trained dataset. The preferred algorithm is configured to develop the 3D model based on a predicted cast, splint, or brace based on paired limbs and body parts. The algorithm is preferably configured to engrave the 3D model with a patient desirable texture or shape or to engrave the 3D model for any deformities, sores or wounds automatically or manually based on a user selection. The preferred algorithm is configured to insert markers into the 3D model for any injuries, medical records and/or prescribed notes with decision-making and natural language processing to customize the 3D model in size, shape, engravement, pattern, length, markers, and/or related features. The algorithm preferably includes AR and VR configured to visualize the 3D model and guide a scanning technique for the patient in a scanning process. The algorithm is preferably configured for feature selection, and any customizable casting parameters including lattice shape, engravements, markers and/or related features. The algorithm integrates a preferred scanning process with additive manufacturing G-code to print the 3D model in the scanning chamber.

Capturing devices of the preferred scanner system include an X-ray integration to overlay a skin surface of the object for feature extraction, bone 3D model and a parametrization system. The capturing devices of the preferred scanner system include feature detection and body part pattern recognition, wherein the capturing devices capture keypoints and an algorithm conducts probability mapping to find features for automated mesh processing including drawing cutting lines, making contours, curvatures, skeleton mapping and/or related features. The preferred algorithm is configured for visualizing a corrected position of the object, wherein the object comprised of a limb of the patient and the algorithm is configured to adjust limb position. The algorithm includes a modified training machine in the preferred embodiments that learns and updates a network, customers' keypoints modification for a cutting line and mesh-processing to improve accuracy for further keypoints detection and probability function. The central processor of the preferred scanner system includes telemedicine capability with a direct uplink of one of images and radiographic image overlay to an x-ray image. A patient's medical records are preferably integrated into the central processor when the scanner system is being utilized to construct a cast, splint, brace or other support for the patient.

The capturing devices of the preferred scanner system include at least one of an x-ray machine, an x-ray generator, an x-ray detector, a medical imager, a radiography machine, a computed tomography ("CT") scanner, a positron emission tomography ("PET") scanner, a single-photon emission computed tomography ("SPECT") scanner, an x-ray tomographer, and/or a backscatter x-ray scanner. The data utilized with the preferred scanner system includes data from the x-ray machine, wherein the data from the x-ray is overlayed by the data from the cameras and lasers to define the 3D model. The central processor is preferably configured to develop an augmented reality file of the 3D model, wherein the 3D model is comprised of a joint of the patient's anatomy. The preferred augmented reality file is configured to facilitate visualization of a corrected position of the injured limb and permits adjustment of the position of the limb. The central processor of the preferred scanner system is configured to facilitate telemedicine by providing direct uplink of the 3D model and data for review by a remote medical professional.

In yet another aspect, the preferred invention is directed to an apparatus to provide multi-entries for a patient's limbs in a scanner system having a scanning chamber. The preferred apparatus includes a transparent glass on a surface of the scanning chamber, a cloth and zippers on a housing surrounding the scanning chamber, a table and a chair designed for the patient to allow inserting the patient's limbs into the scanning chamber from the entries, a hydraulic or a mechanical leveling bed to level a height of the object based on a height of the patient and a rigid cover over the scanning chamber to prevent an ambient light from entering into the scanning chamber. The zippers are configured to function as entries for the patient's limbs into the scanning chamber. The preferred apparatus also includes a moving plane, a first plane connected to the moving plane and a second plane connected to the moving plane. The first and second planes extend generally perpendicularly relative to the moving plane and the moving plane, first plane and second plane are positioned in the scanning chamber. The first and second planes are movable relative to the moving plane to adjust the positioning of cameras and lasers attached to the first and second planes.

A three-dimensional laser scanner device specialized for all objects including body parts such as a finger, hand, forearm, elbow, arm, foot, leg, knee, thigh, shoulder, torso, etc. The laser scanner machine preferably includes a number of capturing devices, lasers, mechanical actuators to move the scanning mechanism, three moving planes containing capturing devices, stationary capturing devices, such as an array of cameras and lasers, shafts, ball bearings, micro switches and related equipment. The laser scanner machine preferably collects the data in the form of 2D photos reflected from the laser beams onto the objects and the correspondent software collects the image data and analyzes it to construct a 3D model of the object or the body part based on software and computing methods with online and offline learning techniques. The included computing method can generate orthopedic casts, braces, splints, molds, templates and related items based on the trained dataset with various related features as deformities, wounds, sores, and patient-related features to reconstruct and visualize the final 3D-model with an appropriate size, type, specific engravements and related features. The physician and technician may also input information to the controller of the laser scanner machine, such as condition of the patient's skin on the scanned body part, location of a bone break or crack and related physiological or conditional features. The preferred laser scanner device is designed to construct the 3D model of the body part in a very short time, limiting involuntary body movements that may damage the real size of a 3D reconstructed body part, which can also be used for designing a customized cast, splint, or brace, or other medical or data collection purpose. The 3D laser scanner device may model an opposite body part, such as the left hand for a right-hand cast or splint, if the subject body part has suffered trauma and has an irregular shape or is swollen. The high speed of the preferred 3D scanner makes the scanning process fast and convenient for the patient while he/she holds the body or body part still for a relatively short time. The preferred 3D scanner can be applied for children where staying still for a relatively short time allows capturing enough reliable data to construct the 3D model of the body part. This high-speed scanning method has the advantage to finish the process before any tremor, movement or vibration in the body part can damage and distort the model. Automated orthosis design, cloud/electronic medical record interface for recording, body part analysis based on patient's clinical features, patient convenience, high speed, mechanical properties output prediction, 3D-printing parameters optimization, cost-effective scanning, and data reliability are preferred features of 3D scanner and method described herein.

In a further aspect, the preferred invention is directed to a scanner system for capturing a 3D model of an object. The scanner system includes a laser and a camera to capture 2D images of the object. The system also includes a tube mounted to a rail, a central processor configured to receive data collected from the laser and the camera and an actuation mechanism configured to move the tube along the rail. The tube is configured to move generally along a travel axis of the rail. The tube includes open first and second tube ends. The laser and camera are mounted inside the tube between the first and second tube ends. The first tube end includes a first continuous ring, and the second tube end includes a second continuous ring. A channel extends through the tube between the first and second rings positioned adjacent the rail in an assembled configuration. The movement of the tube relative to the patient's body part facilitates relatively accurate scanning of the patient's body part, as the body part remains still while the tube moves relative to the body part.

In an additional aspect, the preferred invention is directed to a method of constructing a custom splint, cast or brace based on a pre-printed model, such as a pre-printed hand model. The method includes the steps of storing a plurality of 3D base models, receiving images of a body part of a patient, analyzing the images of the body part with a machine learning algorithm, selecting a fitting 3D base model from the plurality of 3D base models based on the analysis of the images of the body part and manipulating the fitting 3D base model based on the analysis of the images of the body part.

BRIEF DESCRIPTION OF THE SEVERAL VIEWS OF THE DRAWINGS

The foregoing summary, as well as the following detailed description of preferred embodiments of the scanner system, instrument, implant and method of the present disclosure, will be better understood when read in conjunction with the appended drawings. For the purposes of illustrating scanner system, 3D scanning and automated 3D cast and splint design and related methods, there are shown in the drawings preferred embodiments. It should be understood, however, that the application is not limited to the precise arrangements and instrumentalities shown. In the drawings.

DETAILED DESCRIPTION OF THE INVENTION

Figure 1:
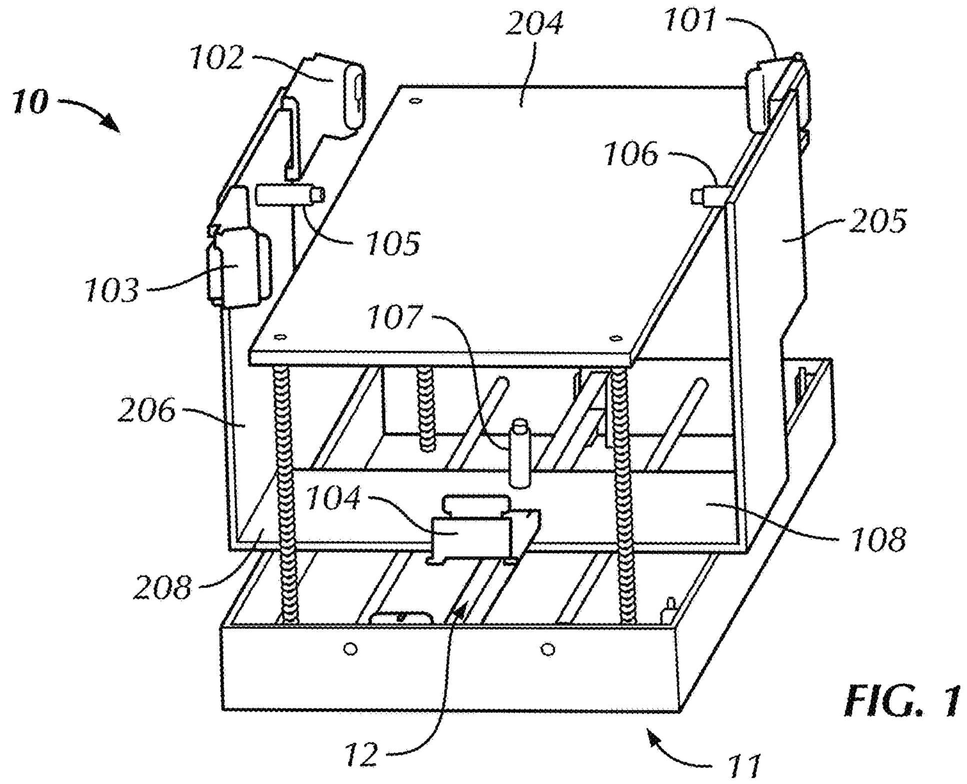
FIG. 1 is a top perspective view of an interior portion of a three-dimensional ("3D") scanner or scanner system in accordance with a first preferred embodiment of the present invention, wherein cameras and lasers of the scanner are shown, and housing components are removed for clarity.
Figure 2:
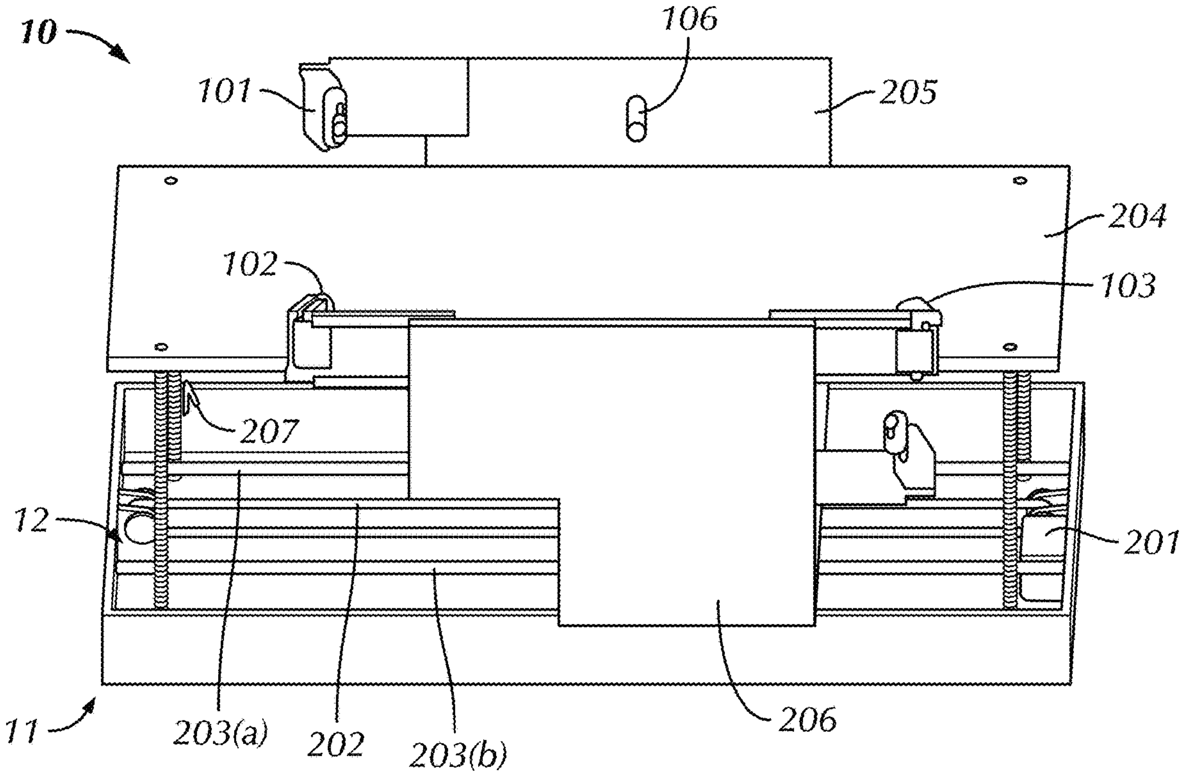
FIG. 2 is side perspective view of the 3D scanner of FIG. 1, wherein mechanical elements of an actuation mechanism are shown.

Certain terminology is used in the following description for convenience only and is not limiting. Unless specifically set forth herein, the terms "a", "an" and "the" are not limited to one element but instead should be read as meaning "at least one." The words "right," "left," "lower" and "upper" designate directions in the drawings to which reference is made. The words "inwardly" or "distally" and "outwardly" or "proximally" refer to directions toward and away from, respectively, the patient's body, or the geometric center of the preferred anatomic three-dimensional scanning and automated 3D cast and splint design, 3D scanner system and related parts thereof. The words "anterior," "posterior," "superior," "inferior," "lateral" and related words and/or phrases designate preferred positions, directions and/or orientations in the human body to which reference is made and are not meant to be limiting. The terminology includes the above-listed words, derivatives thereof and words of similar import.

It should also be understood that the terms "about," "approximately," "generally," "substantially" and like terms, used herein when referring to a dimension or characteristic of a component of the preferred invention, indicate that the described dimension/characteristic is not a strict boundary or parameter and does not exclude minor variations therefrom that are functionally the same or similar, as would be understood by one having ordinary skill in the art. At a minimum, such references that include a numerical parameter would include variations that, using mathematical and industrial principles accepted in the art (e.g., rounding, measurement or other systematic errors, manufacturing tolerances, etc.), would not vary the least significant digit.

Referring to FIGS. 1-10, a first preferred 3D scanner or machine, generally designated 10, and the described actuation mechanism that may be utilized with the scanner 10 is an exemplary description and not meant to be limiting. The first preferred 3D scanner or machine 10 may include nearly any actuation mechanism with a different type of control mechanism, processing units, motors, mechanical elements and other features that facilitate performance of the preferred functions, operation in the normal operating conditions of the first preferred scanner 10 and functioning within the preferred size and shape of the scanner 10. The interface between components of the first preferred scanner 10 that communicate with each other to support operation of the scanner 10 can be in a cable, wireless, Bluetooth, or any similar technologies.

Referring to FIG. 1, the 3D scanner 10 of the first preferred embodiment includes an interior scanning mechanism, which is preferably placed inside a scanning chamber to be in a dark space, away from the ambient lights. The 3D scanner 10 is not so limited and may be operated without a dark space without significantly impacting the operation of the preferred 3D scanner 10. The interior scanning mechanism preferably includes a first or left laser 105, a second or right laser 106 and a third or bottom laser 107 that operate to illuminate the object from multiple angles. The first, second and third lasers 105, 106, 107 radiate a narrow beam to the object positioned within the scanning chamber to reveal points on the object surface in a line by line manner. In addition, in the first preferred embodiment, there are three main cameras 101, 102, 104 to capture points of the object in addition to a backup camera 103. The main cameras 101, 102, 104 are placed in a way that they have preferably the least intersection in their captured set of points. These cameras include a first or right camera 101, a second or left camera 102 and a third or bottom camera 104. The backup camera 103 has a major intersection in the set of captured points with all the main cameras 101 102, 104. The purpose of using the preferred backup camera 103 is to cover blind spots that might be hidden from the view of one or two of the main cameras 101, 102, 104 in some places on the object. The lasers 105, 106, 107 and cameras 101, 102, 104 preferably move together at the same distance from each other during operation based on the functioning of the internal scanning mechanism. The bottom camera 104 and bottom laser 107 are preferably placed on a moving plane 108. In the first preferred embodiment, the moving plane 108 is constructed of a generally C-shaped structural member that supports the cameras 101, 102, 103, 104 and the lasers 105, 106, 107. The moving plane 108 is preferably moved relative to a frame 11 of the scanner 10.

Referring to FIGS. 2, 3, 5 and 6, the interior scanning mechanism includes an actuation mechanism or actuators 12 that drive or control the movement of the moving plane 108, as well as the attached lasers 105, 106, 107 and cameras 101, 102, 103, 104. The actuation mechanism 12 of the first preferred embodiment includes a motor 201, such as a stepper motor 201, that operates after receiving an initiation command from a processing unit or central processor 503. The moving plane 108 is preferably connected to a belt or driving mechanism 202 that is driven by the motor 201. As the motor 201 is actuated by the central processor 503, the belt 202 starts to turn around a roll bearing 302 as the stepper motor 201 starts to work. The belt 202 is coupled to the moving plane 108 with a coupling component 304, such as a clamp, magnet, clip or other fastening mechanism or assembly that secures the belt 202 to the moving plane 108. Thus, when the stepper motor 201 starts to work, the moving plane 108 preferably moves on a linear track guided by the shafts 203(*a*), 203(*b*), although the moving plane 108 is not so limited and may otherwise move, such as in rotation or other moving paths to capture images of the object in the interior of the scanner 10. The actuation mechanism 12 also preferably includes ball bearings or fittings 301(*a*), 301(*b*), 301(*c*), 301(*d*) that are separately shown in FIG. 3. The ball bearings 301(*a*), 301(*b*), 301(*c*), 301(*d*) are connected to the moving plane 108 and move along shafts 203(*a*), 203(*b*) that are attached to the frame 11 to guide the preferred linear movement of the bottom plane 108. The bottom plane 108 preferably includes a first or right plane 205, a second or left plane 206 and a third or base plane 208. The base plane 208 is preferably connected to the coupling component 304 to drive movement of the bottom plane 108. The third or bottom laser 107 and the third or bottom camera 104 are preferably connected to the third or base plane 208, the second or left camera 102, the backup camera 103 and the first or left laser 105 are connected to the second or left plane 206 and the first or right camera 101 and the second or right laser 106 are attached to the first or right plane 205 in the first preferred embodiment. A microswitch 207 is preferably placed at an end of the scanner 10 or at an end of the frame 11 relative to the movement of the moving plane 108 to control the movement of the moving plane 108. A lid 204, which may be constructed of a transparent structural member, such as a Plexiglas or generally transparent sheet, is preferably placed at a top of the scanner 10 and defines a portion of the frame 11. The lid 204 preferably permits visualization of the anatomical body part or object that is placed into the scanner 10 during use.

Figure 3:
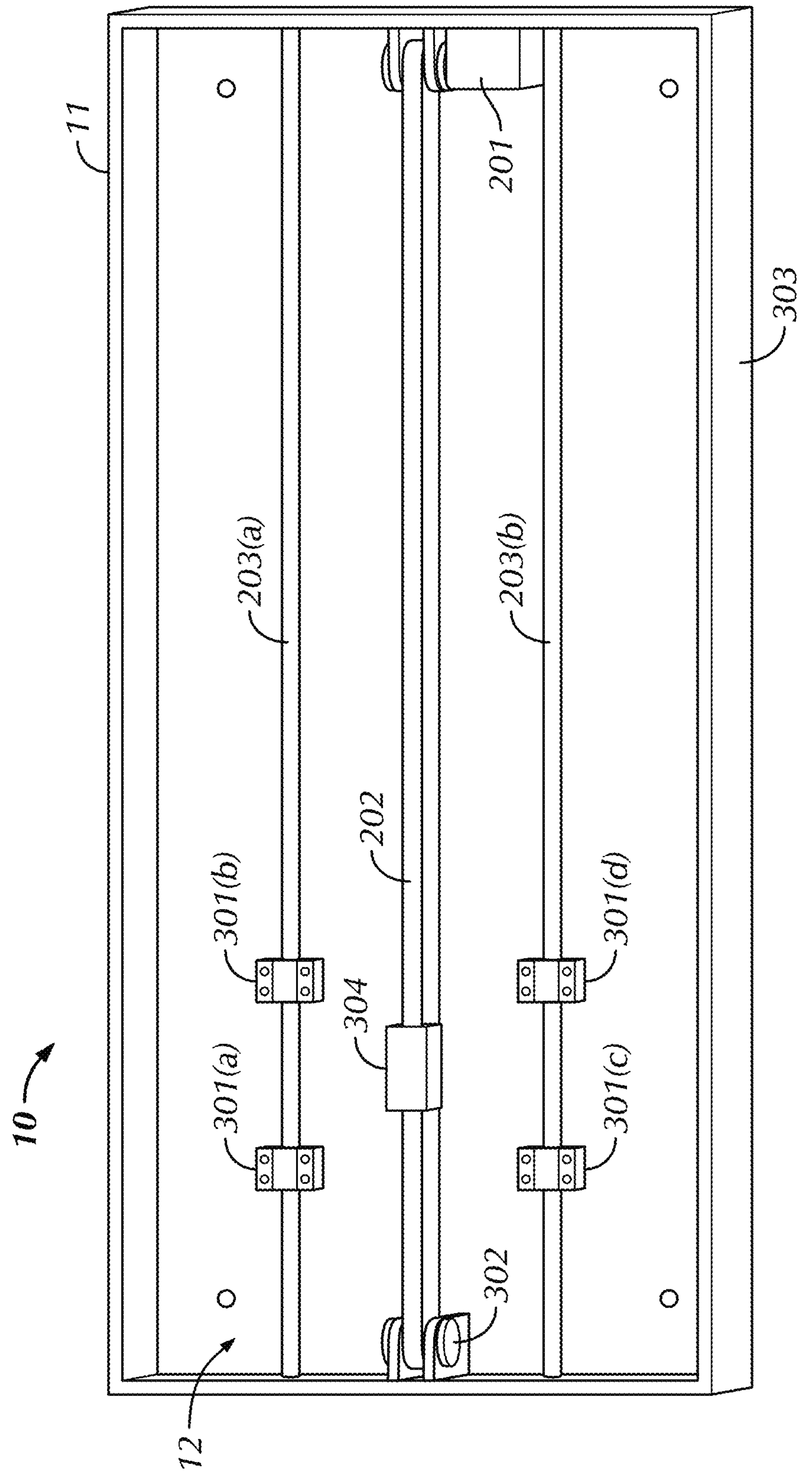
FIG. 3 is a top perspective view of an actuation structure of the 3D scanner of FIG. 1, wherein cameras, lasers, moving planes and a scan chamber floor are excluded for clarity.

Referring to FIG. 3, the mechanical components of the scanner 10, excluding the moving plane 108 and the first or right and second or left planes 205, 206 and the upper portion of the frame 11, includes the motor 201, which may be comprised of the stepper motor 201, the roll bearing 302 and the two shafts 203(*a*), 203(*b*). The belt 202 is driven by the stepper motor 201 and guided by the roll bearing 302. The ball bearings or fittings 301(*a*), 301(*b*), 301(*c*), 301(*d*) guide the linear movement of the moving plane 108 on the shafts 203(*a*), 203(*b*). The frame 11 supports the stepper motor 201, the shafts 203(*a*), 203(*b*) and the roll bearing 302.

Figure 4:
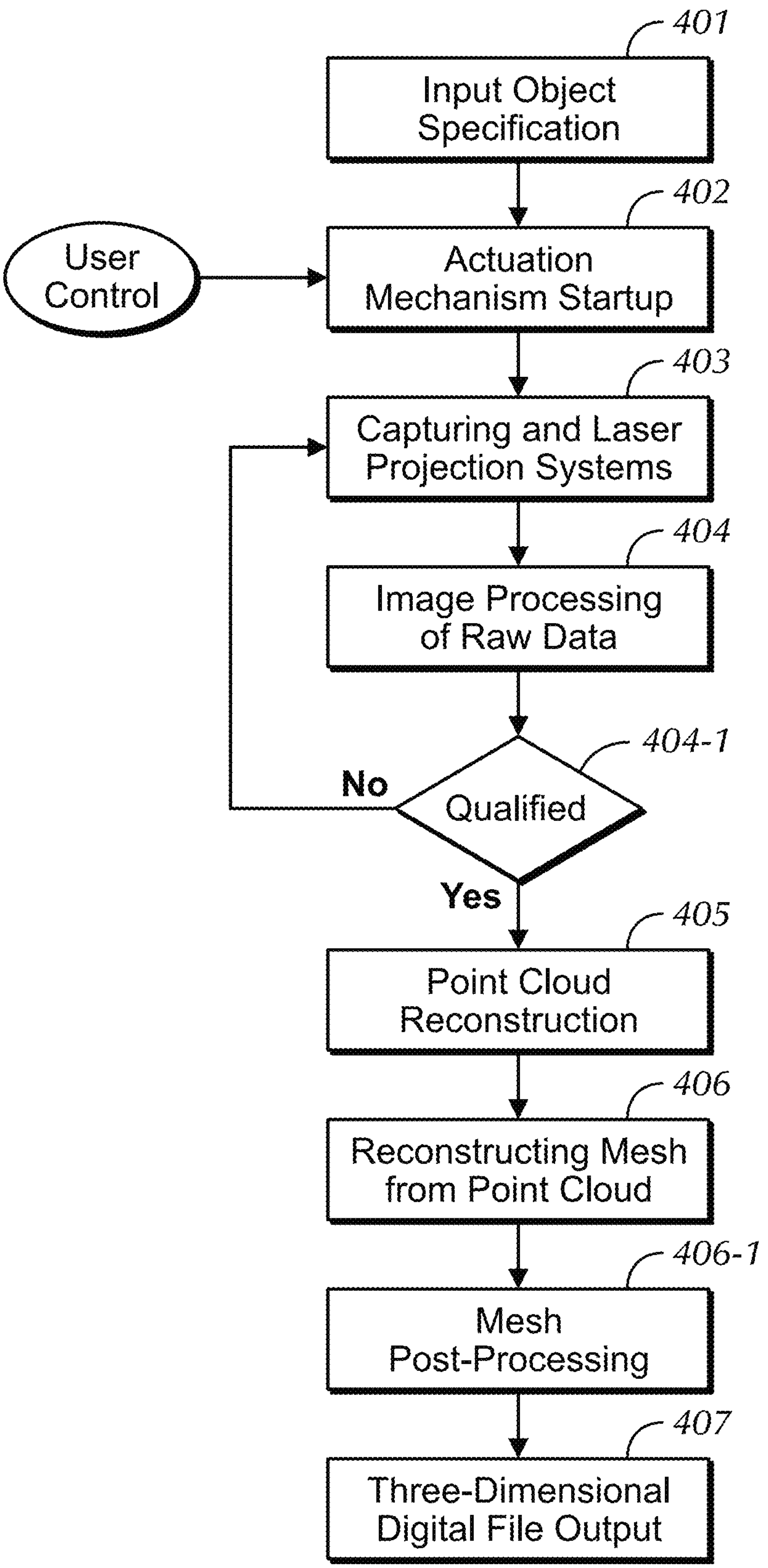
FIG. 4 is a block diagram representation of a 3D scanning process that may be utilized with the 3D scanner of FIG. 1.
Figure 5:
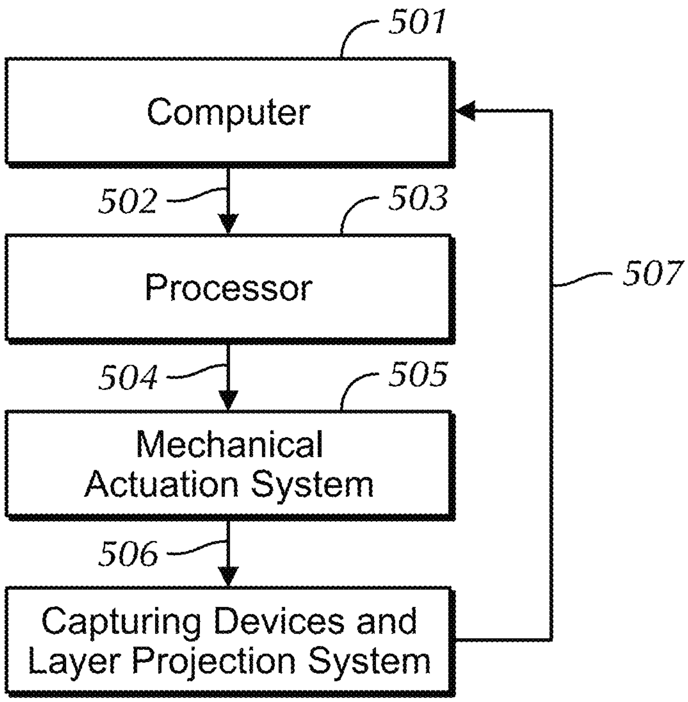
FIG. 5 is a block diagram representation of data flow from a computer or central server/processor to the 3D scanner of FIG. 1.
Figure 6:
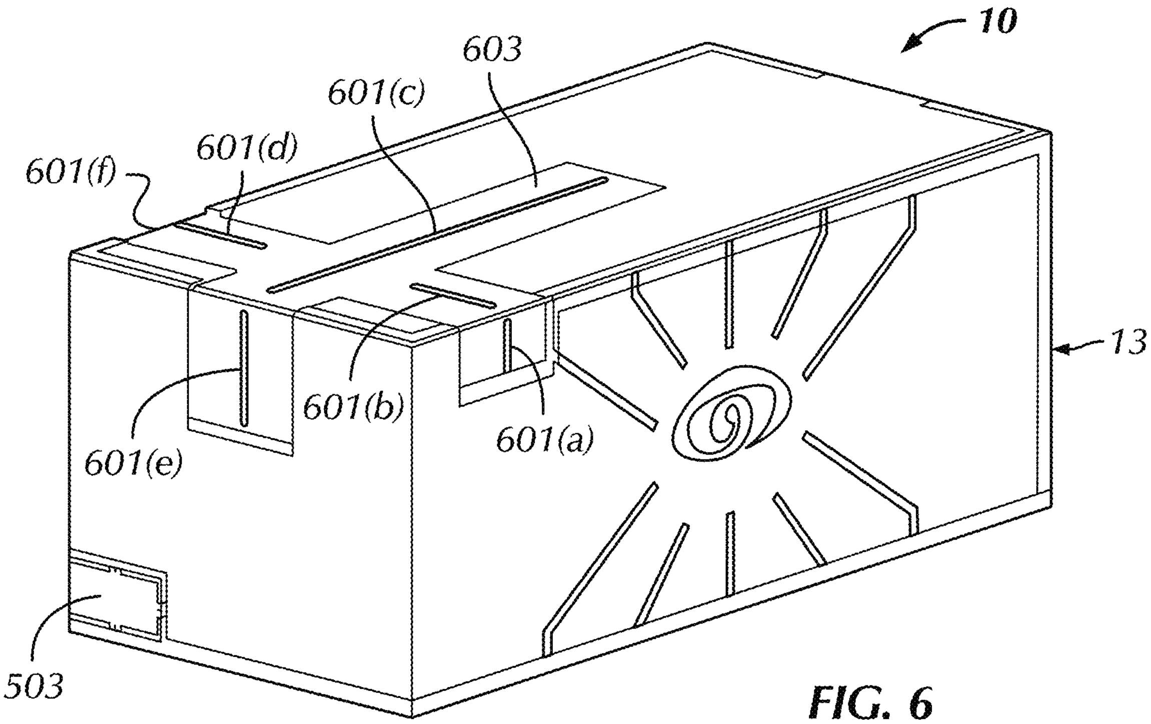
FIG. 6 is a side perspective view of an exterior housing of the 3D scanner of FIG. 1, wherein zippers or portholes for insertion of a patient's arm, foot, and other target objects or anatomy are highlighted.

Referring to FIGS. 3-5, during operation of the scanner 10 in a preferred first step 401, the user enters the patient's specifications such as the left or right foot or arm, age, name, and related patient information into the software of the scanner 10, which is preferably housed in the processing unit or central server 503. After pressing a scan button, the scanning process starts. The processing unit or central server 503 of the computer 501 sends commands to the scanner 10. The processing unit or central server 503 may be comprised of a wireless microcontroller that is connected to the scanner 10 and drives the stepper motor 201. The cameras 101, 102, 103, 104 and the lasers 105, 106, 107 start to move in the scanning area around the patient's limb or the object and along the linear track defined by the shafts 203(*a*), 203(*b*). This actuation mechanism startup 402 step is driven by the processing unit or central processor 503. The lasers 105, 106, 107 illuminate the object with laser beams and the images are captured using the cameras 101, 102, 103, 104. An interface 507 then sends the collected data to the processing unit 503 and the scanner software. In the software, the raw data is processed in an image processing or raw data step 404 so that the 2D images are converted to the 3D coordinates and the point cloud of the object. Following the initial scan, the central server 503 analyzes the collected data to determine if there are potential missing or underdeveloped areas of the object. If the central server 503 determined there are missing points in the point cloud, the software analyzes and constructs the parts of the missing points on the object. The central server or processor 503 then refers to collected data from the backup camera 103 and preferably covers the missing parts of the point cloud of the object with the data of the backup camera 103 to edit the point cloud in the point cloud reconstruction step 405. In an analysis of the object model or qualified step 404-1, if the output does not satisfy predetermined constraints, potentially including resolution, object size and related constraint, an error will notify the user control to perform the scanning again and the central server 503 will direct the scanner 10 back to the capturing and laser projection system step 403. After this potential point cloud modification, the constructed file is converted to a 3D mesh from point cloud in a point cloud step 406, the mesh is further processed in a mesh post-processing step 406-1 and the 3D mesh is finalized in a 3D digital file output step 407 so that the mesh can be exported in the desired format to the user. The mesh file is then saved in the central server 503 and classified automatically considering the specifications of the patient. The mesh post-processing step 406-1 is to perform the mesh processing including smoothing, outer base design to make orthopedic casts on the specified surface on the mesh, locking mechanism insertions, engraving shapes, and basic processing as mesh subtractions, intersections, and related steps. This mesh post-processing step 406-1 can be performed automatically or manually. The sample Pseudo Code for this process is described in the followings:

A preferred and exemplary pseudocode for the 3D scanner 10 may include the following steps:

1. Capture videos from all preferred cameras 101, 102, 103, 104;
2. Convert videos to multiple frames;
3. Do the followings for each one of the frames?
   - 3.1. gray=cv2.cvtColor (image,cv2.COLOR_BGR2-GRAY)
     (convert the color photo into black and white)
   - 3.2. thresh2=cv2.threshold (gray, 127, 255, cv2.THRESH_BINARY_INV)
     (set a threshold for dividing the pixels into black and white)
   - 3.3. edges=cv2.Canny(thresh2, 50, 150, aperture Size=3)
     (detect the edges)
   - 3.4. Perspective Transform of the edges (to attain the real XYZ coordinates of the object).
   - 3.5. Noise reduction.
4. Attain the circumferences around all of the slices of the object in each frame by attaching the processed images (in task 3) of all the cameras to shape the point cloud of each object slice.
5. Attach the coordinates of slices points to make the complete point cloud.
6. Search the point cloud to detect the regions in which the density of the points is not sufficient. (the missing point regions) 7. Do task 3 for the backup camera(s).
8. Find the missing points by referring to the backup data attained from the backup camera(s).
9. Add the required backup data to the main point cloud.
10. Delete the extra points.
11. Reduce noise.
12. Calculate faces according to the coordinates of the point cloud.
13. Calculate normal vectors according to the coordinates of the point cloud.
14. Reconstruct a mesh using the normal vectors, faces, and vertices of the point cloud.
15. Automated mesh inspection and modification.
16. Show the three-dimensional model of the object to the user.

Referring to FIGS. 1-3 and 5 the scanner 10 interfaces with the central server or processor 503 initially after the user depresses the start button or by the start command. The start command is sent to the central server 503, which may include a microcontroller, through a specified protocol of communication from the computer 501 to the central server 503 in a communication step 502. The central server 503 drives the stepper motor 201 or the mechanical actuation system 505 in a driver step 504. The stepper motor 201 starts running, the lasers 105, 106, 107 and cameras 101, 102, 103, 104 are activated through a synchronization command step 506 that is driven by the central server 503. After capturing 2D images of the object, the cameras 101, 102, 103, 104 send the raw data of the acquired data to the computer 501 and central server 503 through a communication mechanism or method 507, such as cables, wireless communication or other communication systems or methods.

Referring to FIGS. 1-3 and 6, the scanner 10 may include a housing 13 constructed of a relatively transparent material, although not so limited and the housing 13 may be opaque, for viewing the body part or object during the capturing and laser projection systems step 403 and any other steps where the object is within the housing 13 and the user may want to observe the body part or object. The housing 13 may include zippers or portholes 601(*a*), 601(*b*), 601(*c*), 601(*d*), 601(*e*), 601(*f*) from which the object, such as an arm, foot or any other object is entered into the scanning chamber. The zippers 601(*a*), 601(*b*), 601(*c*), 601(*d*), 601(*e*), 601(*f*) preferably make it comfortable for the patients to enter their arm, foot or any other body part or object from any entry into the housing 13. A specialist, the user or the patient can choose the most convenient entry based on the desired scanning body limb and patient comfort. By positioning and orienting all of the zippers 601(*a*), 601(*b*), 601(*c*), 601(*d*), 601(*e*), 601(*f*), the user has a significant set of options to decide where to enter the limb or the object into the scanning chamber. The zippers 601(*a*), 601(*b*), 601(*c*), 601(*d*), 601(*e*), 601(*f*) and their location are not limited to the zippers 601(*a*), 601(*b*), 601(*c*), 601(*d*), 601(*e*), 601(*f*) shown in FIG. 6 and may be otherwise designed and configured for relatively convenient insertion of the body part or object into the housing 13 for scanning. For example, a front side zipper 601(*e*) may be the best option for entering a patient's foot into the scanning chamber, in order to guarantee the full-size scanning of the patient's foot. The zippers 601(*a*), 601(*b*), 601(*c*), 601(*d*), 601(*e*), 601(*f*) may be incorporated into or attached to the housing 13 by a cloth 603 that makes the entry into the housing 13 more flexible and accommodates the use of the zippers 601(*a*), 601(*b*), 601(*c*), 601(*d*), 601(*e*), 601(*f*). A processing unit is preferably comprised of the central server 503, a driver for the stepper motor 201, camera cables and other electrical components. The zippers 601(*a*), 601(*b*), 601(*c*), 601(*d*), 601(*e*), 601(*f*) of the first preferred embodiment include a left side zipper 601(*a*), a left side top zipper 601(*b*), a top zipper 601(*c*), a right side top zipper 601(*d*), the front side zipper 601(*e*) and a right side zipper 601(*f*), although the housing 13 is not limited to these preferred zippers 601(*a*), 601(*b*), 601(*c*), 601(*d*), 601(*e*), 601(*f*) and may include less or more zippers or portholes 601(*a*), 601(*b*), 601(*c*), 601(*d*), 601(*e*), 601(*f*), as well as alternative access structures, systems or mechanisms, such as a self-scaling port, swinging door or other access systems, mechanisms or methods without significantly impacting the structure or function of the preferred scanner 10.

Referring to FIG. 7, the scanner 10 may utilize a trained deep Convolutional Neural Network ("CNN") or related system or method that predicts the 3D-Model based on the collected data from the 2D-images. The preferred CNN is utilized to reconstruct an orthopedic cast, brace, and/or splint with the 2D images captured from the lasers 105, 106, 107 and cameras 101, 102, 103 104. In addition, the central server 503 may also use the input images to detect wounds, sores, deformities, anomalies and related features of the object, preferably a patient's body part, which may then be utilized to reconstruct the orthopedic casts in a customized manner to conform to the input object features. The wounds, sores or deformities may be comprised of swelling, burns, lacerations or other anomalies of the object. The algorithm of the central server 503 is preferably used to train the preferred scanner 10, as is described below. Activation function, loss function, model type and array sizes can be varied based on the input features:

1. Collect data set of images including hand models, sores, wounds, and deformities;
2. Split the train and test dataset;
3. Training the machine with the following code:

```
model=Sequential( )
model.add(Conv2D(32, kernel_size=(5, 5), strides=(1, 1),
activation='relu',
input_shape=input_shape))
model.add(MaxPooling2D(pool_size=(2, 2), strides=(2, 2)))
model.add(Conv2D(64, (5, 5), activation='relu'))
model.add(MaxPooling2D(pool_size=(2, 2)))
model.add(Flatten ( ))
model.add(Dense(1000, activation='relu'))
model.add(Dense(num_classes, activation='softmax'))
model.add(Flatten ( ))
model.add(Dense(1000, activation='relu'))
model.add(Dense(num_classes,
activation='softmax')); and
```

4. Validation and function fitness

```
model.compile
(loss=keras.losses.categorical_crossentropy,
optimizer=keras.optimizers.SGD (lr=0.01), metrics=['accuracy']).
```

In the next preferred step, based on the input image or 3D-model the following code is preferably processed:

5. Based on step 3, the output class of the input image is detected;
6. Based on the output class, rules and features as size, type of the cast, engravements and etc. will be applied on the 3D-Model of the scanned object; and
7. Reconstructing the output 3D-file based on the detected features.

Figure 7A:
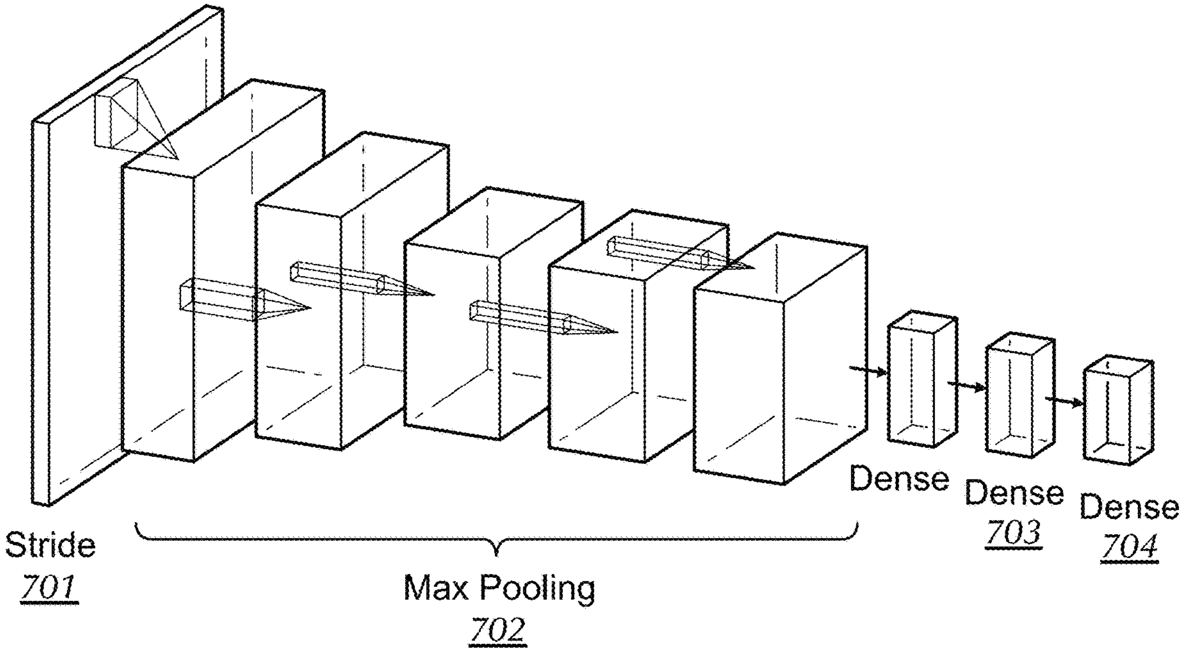
FIG. 7A is representation of a deep convolutional neural network to generate a 3D-object based on similar trained 3D-scanned objects that may be used with the 3D scanner of FIG. 1.

Referring to FIG. 7A, a stride 701 is a layer including human features of deformities, sores, wounds and related features and a max-pooling 702 is a discretization down-sampling process to reduce the dimensionality of input data from the cameras 101, 102, 103, 104 and the lasers 105, 106, 107 to make features contained in the sub-regions binned. The preferred scanner 10 includes three dense networks 703, although the scanner 10 is not so limited, as described herein that preferably generate the output which is preferably an array of output classes 704.

Figure 7B:
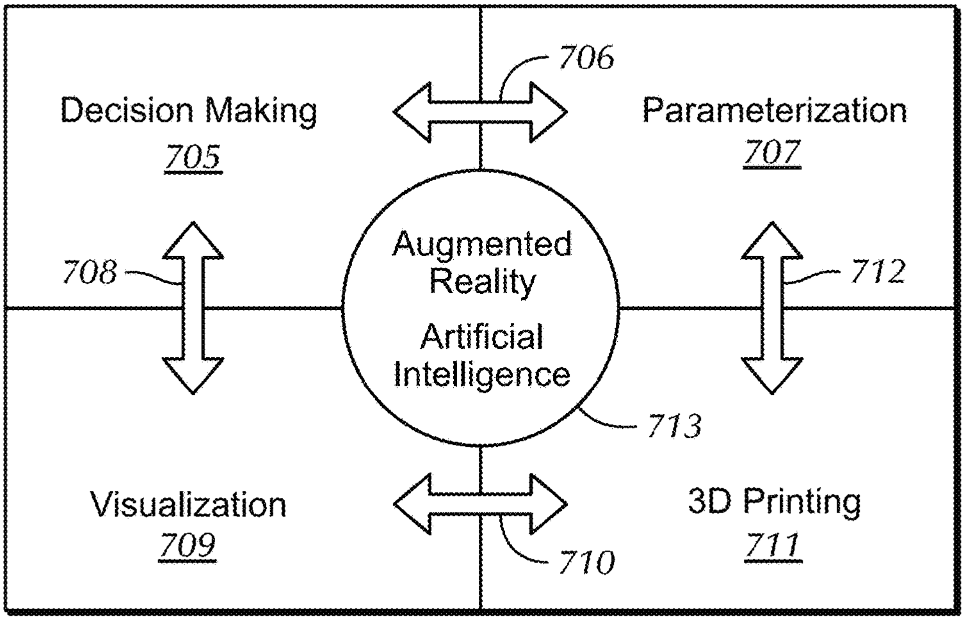
FIG. 7B is a flow diagram of four included modules in an artificial intelligence and augmented reality core that may be utilized with the 3D scanner of FIG. 1.
Figure 8:
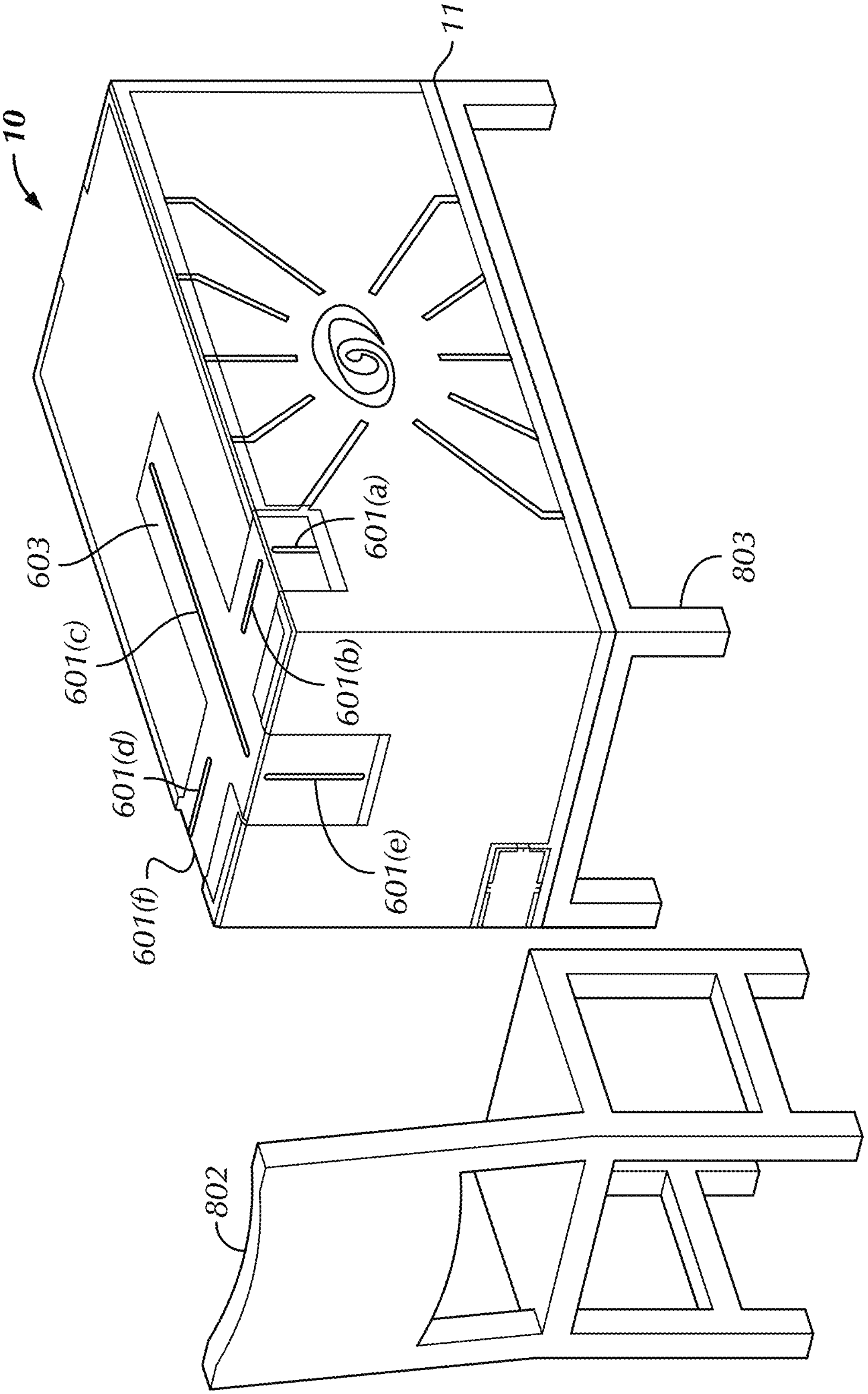
FIG. 8 is a side perspective view of a housing of the 3D scanner of FIG. 1, wherein components that facilitate how patients can comfortably put their hands or feet inside the scanning chamber are represented.

Referring to FIG. 7B, the connection of four main parts including decision-making, parametrization, visualization, and 3D-printing is utilized with the preferred augmented reality/artificial intelligence of the preferred scanner 10. The process is preferably controlled by an Artificial Intelligence and Augmented Reality core 713. Parameterization 707 is preferably utilized and is comprised of a technique used to set-up the orthopedic cast or splint, such as length, mechanical properties, 3D printing parameters with multi-objective optimization, many-objective optimization, mass customization, reinforcement learning, and optimal control theories.

A decision making algorithm 705 is preferably used to adjust the 3D cast setting as length, mechanical properties, medical records, 3D-printing parameters, shape engravements and related features for each designed cast with the fuzzy system and reinforcement learning to update its parameters.

Casting factors as the place of engravements, lattice shapes, length, shape, type of the splint, cast or brace, lock insertions, boundary surfaces on the cast are each, preferably pre-defined based on the medical records, prescription and patient-specific customization on the physical shapes. A fuzzy system is known as a robust algorithm in decision making with a hybrid of a neural network to update its rules. Adaptive Network-Based Fuzzy Inference System ("ANFIS") may be utilized with the preferred scanner 10 to predict the above parameters with a nonlinear mapping. The challenge with ANFIS algorithm is the selection of the inputs, membership functions, inference engine to make a satisfied predictive performance for this system. This can be done in the following steps:

1. batch size and training epochs;
2. optimization algorithm learning rate and momentum;
3. network weight initialization;
4. activation function in the hidden layer;
5. dropout regularization; and
6. the number of neurons in the hidden layer.

The following code is a preferred python implementation for the convergence of this ANFIS that may be utilized with the scanner 10:

```
while (epoch < epochs) and (convergence is not True):
  #layer four: forward pass
  [layerFour, wSum, w] = forwardHalfPass(self, self.X)
  #layer five: least squares estimate
  layerFive = np.array(self.LSE(layerFour,self. Y,initialGamma))
  self.consequents = layerFive
  layerFive = np.dot(layerFour,layerFive)
  #error
  error = np.sum((self. Y-layerFive.T)**2)
  print('current error: '+ str(error))
  average_error = np.average(np.absolute(self.Y-layerFive.T))
  self.errors = np.append(self.errors,error)
  if len(self.errors) != 0:
    if self.errors[len(self.errors)-1] < tolerance:
    convergence = True
```

The backpropagation may be used to update the neural network rules based on the output errors for the preferred scanner 10, as follows:

```
  # back propagation
  if convergence is not True:
    cols = range(len(self.X[0,:]))
    dE_dAlpha = list(backprop(self, colX, cols, wSum, w, layerFive) for
colX in range(self.X.shape[1]))
  if len(self.errors) >= 4:
    if (self.errors[−4] > self.errors[−3] > self.errors[−2] > self.errors[−1]):
      k =k * 1.1
  if len(self.errors) >= 5:
    if (self.errors[−1] < self.errors[−2]) and (self.errors[−3] < self.errors[−2])
and (self.errors[−3] < self.errors[−4]) and (self.errors[−5] > self.errors[−4]):
      k = k * 0.9
```

In a preferred final stage, it is used to update the membership functions of the fuzzy system, including the variance and average of each gaussian membership function. The relation of the parameterization 707 of the objects and the decision making algorithm 705 are the gaussian membership functions which are transformed 706 into the fuzzy engine.

In order to conduct the visualization 709, the output of construction 708 of the cast or splint, an Augmented Reality ("AR") is preferably utilized. In the following steps it guides and visualizes the output of the AI reconstructing machine, preferably as follows:

Target Surface Recognition: Feature Extractor, transform and matching

```
img = cv2.imread('scene.jpg',0)
# Initiate ORB detector
orb = cv2.ORB_create( )
# find the keypoints with ORB
kp = orb.detect(img, None)
# compute the descriptors with ORB
kp, des = orb.compute(img, kp)
# draw only keypoints location,not size and orientation
img2 = cv2.drawKeypoints(img, kp, img, color=(0,255,0), flags=0)
cv2.imshow('keypoints',img2)
cv2.waitKey(0)
```

Homography Estimation: Random Sample Consensus ("RANSAC")

```
# assuming matches stores the matches found and
# returned by bf.match(des_model, des_frame)
# differenciate between source points and destination points
src_pts = np.float32([kp_model[m.queryIdx].pt for m in
matches]).reshape(-1, 1, 2)
dst_pts = np.float32([kp_frame[m.trainIdx].pt for m in
matches]).reshape(-1, 1, 2)
# compute Homography
M, mask = cv2.findHomography(src_pts, dst_pts, cv2.RANSAC, 5.0)
```

Derive Projection

```
def projection_matrix(camera_parameters, homography):
""
  From the camera calibration matrix and the estimated homography
  compute the 3D projection matrix
  ""
# Compute rotation along the x and y axis as well as the translation
homography = homography * (-1)
rot_and_transl = np.dot(np.linalg.inv(camera_parameters),
homography)
col_1 = rot_and_transl[:, 0]
col_2 = rot_and_transl[:, 1]
col_3 = rot_and_transl[:, 2]
# normalise vectors
1 = math.sqrt(np.linalg.norm(col_1, 2) * np.linalg.norm(col_2, 2))
rot_1 = col_1 / l
rot_2 = col_2 / l
translation = col_3 / l
# compute the orthonormal basis
c = rot_1 + rot_2
p = np.cross(rot_1, rot_2)
d = np.cross(c, p)
rot_1 = np.dot(c / np.linalg.norm(c, 2) + d / np.linalg.norm(d, 2), 1 /
math.sqrt(2))
rot_2 = np.dot(c / np.linalg.norm(c, 2) - d / np.linalg.norm(d, 2), 1 /
math.sqrt(2))
rot_3 = np.cross(rot_1, rot_2)
# finally, compute the 3D projection matrix from the model to the
current frame
projection = np.stack((rot_1, rot_2, rot_3, translation)).T
return np.dot(camera_parameters, projection)
```

Project and Draw the Model

```
def render(img, obj, projection, model, color=False):
  vertices = obj.vertices
  scale_matrix = np.eye(3) * 3
  h, w = model.shape
  for face in obj.faces:
    face_vertices = face[0]
    points = np.array([vertices[vertex - 1] for vertex in
face_vertices])
    points = np.dot(points, scale_matrix)
     # render model in the middle of the reference surface. To do so,
     # model points must be displaced
    points = np.array([[p[0] + w / 2, p[1] + h / 2, p[2]]
for p in points])
    dst = cv2.perspectiveTransform(points.reshape(-1, 1, 3),
projection)
    imgpts = np.int32(dst)
    if color is False:
      cv2.fillConvexPoly(img, imgpts, (137, 27, 211))
    else:
      color = hex_to_rgb(face[-1])
      color = color[::-1] # reverse
      cv2.fillConvexPoly(img, imgpts, color)
  return img
```

Referring to FIGS. 1-3, 6 and 8, patients are preferably able to sit on a chair 802 and scan their feet from an entry through the front side zipper 601(*e*) or insertion of other body parts through the other zippers 601(*a*), 601(*b*), 601(*c*), 601(*d*), 601(*f*). For patients with difficulties, the scanner 10 may be placed on a long table or other support structure.

The described scanner 10 is preferably configured for fast, high-precision, cost-effective, reliable, and convenient use. The scanner 10 of the first preferred embodiment is configured for use in orthopedic applications to scan body limbs and other anatomy of a patient. Most scanners are designed to have one or two of the mentioned advantages, but the described preferred scanner 10 in the present invention is preferably configured to cover orthopedic applications in body limb scanning. The described parameters are preferred parameters and features of an orthopedic 3D scanner.

The preferred scanner 10 is configured for scanning the arm, forearm, foot, fingers, torso and other body limbs of the body to construct a 3D model of the scanned object so that clinicians can design and 3D print a costume-made cast, splint or orthopedic brace. However, the application is not confined to scanning body limbs. In addition, it is possible to scan any other object as long as the object can fit inside the scanning chamber of the scanner 10 and the scanner 10 is otherwise able to scan the object.

Figure 9:
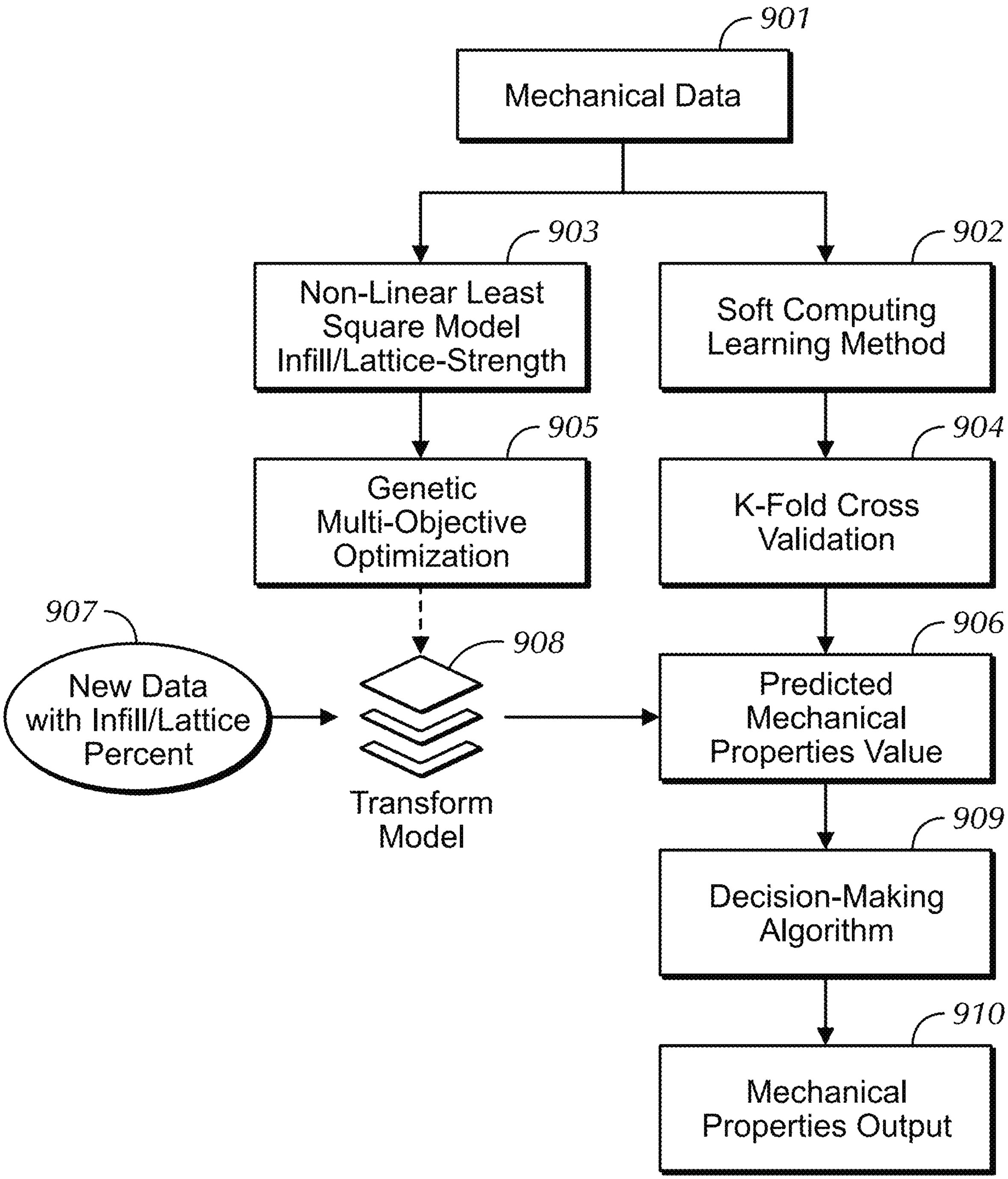
FIG. 9 is a block diagram of mechanical properties prediction and 3D-printing parameters optimization learning algorithm that may be utilized with the 3D scanner of FIG. 1.

Referring to FIG. 9, the scanner 10 preferably includes an optimization step 905 and mechanical properties prediction algorithms. This algorithm is utilized to optimize 3D-printing parameters as infill, lattice, shell size, raster angle, and other factors that are preferred for the scanner 10. In addition, optimization step 905 preferably predicts mechanical properties such as flexure, shear, compressive strength, roughness and related features. The description code is an instance of optimization and mechanical prediction of infill and lattice-flexural strength (3D-printing parameters). The functions and algorithms are not limited to the specific function, loss function, optimization, online or offline learning methods. The general soft computing techniques in this algorithm can be fuzzy, genetic, neural network, probabilistic reasoning, and any hybrid methods, such as the soft computing learning method step 902 or the parameterization step 707.

Measuring a distance is a common criteria utilized in the field of optimal fitting. Numerical methods are typically utilized for these criteria minimization. Curve fitting is preferably used to find a fit for the collected data. Due to the collected data both in Infill and Lattice groups, two figures are proposed to illustrate the force-infill and force-lattice curves in a non-linear least square model infill/lattice strength step 903. There are various non-linear models to find the best fit such as power series, Gaussian, polynomial, Fourier, exponential and related techniques. A power series with two terms is used in this curve-fitting, preferably defined by the following function:

$$f(x)=a*x^b+c$$

Based on the above functions, two objective functions are preferably formulated to minimize Genetic Multi-Objective Optimization ("MOO") loss and satisfy the problem constraints in this algorithm which can be different based on the defined problems. Nondominated Sorting and Genetic Algorithm ("NSGA") may be utilized in Evolutionary Algorithms ("EA") that are preferably utilized to solve multi Pareto-optimal without converting to single-objective problems. However, disadvantages of this algorithm can be mentioned as high computational complexity of nondominated sorting, lack of elitism, and the need for specifying the sharing parameter $\partial_{share}$. The NSGA-II algorithm, therefore, was developed to solve the criticisms in the first version of NSGA. This technique, however, can be replaced by any other optimization algorithms for the genetic multi-objective optimization step 905.

The preferred algorithm for NSGA-II MOO is described in the followings:

1. Parametrizing the MOO functions including the maximum number of generations with size N, the mutation rate of $\mu$, crossover rate of $\sigma$, number of individuals I, number of elites, and control variable limits;
2. Generate the random initial population $N^0$ under the objective constraints;
3. For each individual at generation N t, run the loss function comprised of objective;
4. Create offspring population offspring t+1 from N t at the time of t by crossover and mutation operators;
5. Perform non-dominant sorting to identify the points of optimal Pareto front PFi =1, 2, . . . , m;
6. Restricting the number of individuals from the controlled elitism concept to maintain a pre-distributed number of individuals with an r-value of 0.4; and
7. if t=N, then the process is stopped. Otherwise, it does another loop with an increment in the value of t. Individuals in N t is the Pareto-optimal front.

One of the soft computing methods which may be used with the scanner 10 of the preferred invention as a learning method is a Neural Network, preferably in a soft computing learning method step 902. An Artificial Neural Network ("ANN") is a soft computing method inspired by the biological neural network. In ANNs, different layers including the different number of interconnected neurons perform special functions. This network consists of three layers of the input, hidden, and output layers. Hidden layers aim to relate the input and output nodes. The process of building the ANN structure is to update the initial weights of neurons. The widely used mathematical chain method for updating neuron's weights is called backpropagation that computes layers gradient iteratively. The number of layers, activation function, regression or classification can be varied based on the type of the desired output and input data features.

In this proposed neural network architecture of the soft computing learning method step 902, it preferably has five layers including one input with two nodes (infill and lattice percentage), one output with one node (flexural strength), and three hidden layers, although this configuration is preferred the specific configuration not limiting. The type of classifier is preferably "sequentially" performed with the activation function for the input layer in a "relu" function with a uniform kernel initialization. The second layer preferably utilizes the relu activation function and a uniform kernel initialization. The third layer is preferably a dropout layer to cut-off to reduce the overfitting in this regularization network. This layer increases the network structure robustness of the inputs.

The preferred last layer, which is an output layer, is preferably a softmax activation function. This structure may utilize an ADAM optimizer and a categorical cross-entropy function to generate multi classes in this network. This transforms the regression to logistic regression for the output flexural strength prediction.

Cross entropy can be used in machine learning algorithms as a performance measure, as well as with the preferred scanner 10. It is used based on the input probability and the given probability distribution to predict the true value of output. Logistic regression is used to classify the observed data into the possible classes. This can be categorized into two possible methods of binary classification and categorical classification. The categorical classification is used for more than two labels in the output. In this problem, three categories of low, medium, and high shear strength categories may be considered as a preferred categorization but is not limiting. In multi-class classification, a hot encoder is used to convert the multiple output labels into binaries. Afterward, the categorical cross-entropy performance measure is placed in the last neural network layer.

In this proposed structure shown as the non-linear least square model infill/lattice strength step 903, two non-linear least square models are fitted with power series for the input mechanical data. Those functions including infill-force and lattice-force are optimized by the genetic multi-objective algorithm. In the parallel network, mechanical data is used to train the classification neural network. Then, the network is preferably validated with a K-fold cross-validation algorithm in a K-fold cross-validation step 904.

This hybrid algorithm is used with the preferred scanner 10 to predict the output strength of new infill and lattice percent with PLA material in a predicted mechanical properties value step 906. A transform model step 908 on MOO is preferably utilized to find the infill or lattice percent equivalents of the new data. Therefore, the solution space in the preferred embodiments may be represented, as follows:

$$H=\{(H_{infill},H_{lattice}),(H_{infill},H_{infill_{equivalent}}),(H_{lattice_{equivalent}},H_{lattice}),(H_{lattice},H_{lattice_{equivalent}})\}$$

In the above preferred array, $H_{infill_{equivalent}}$ and $H_{lattice_{equivalent}}$ are the substantially the same as infill or lattice percent respectively which are preferably determined via genetic MOO. The classes of similar strength are preferably automatically predicted by the trained neural network to find similar classes. The decision-making algorithm 909 uses the most voted class between the four above classes (H) to predict an output strength class of mechanical properties output 910.

```
options=optimoptions('gamultiobj','PlotFcn',
    {@gaplotpareto,@gaplotscorediversity});

x=gamultiobj(fitnessfcn, 1, [], [], [], [],lb,ub,options);
```

Figure 10:
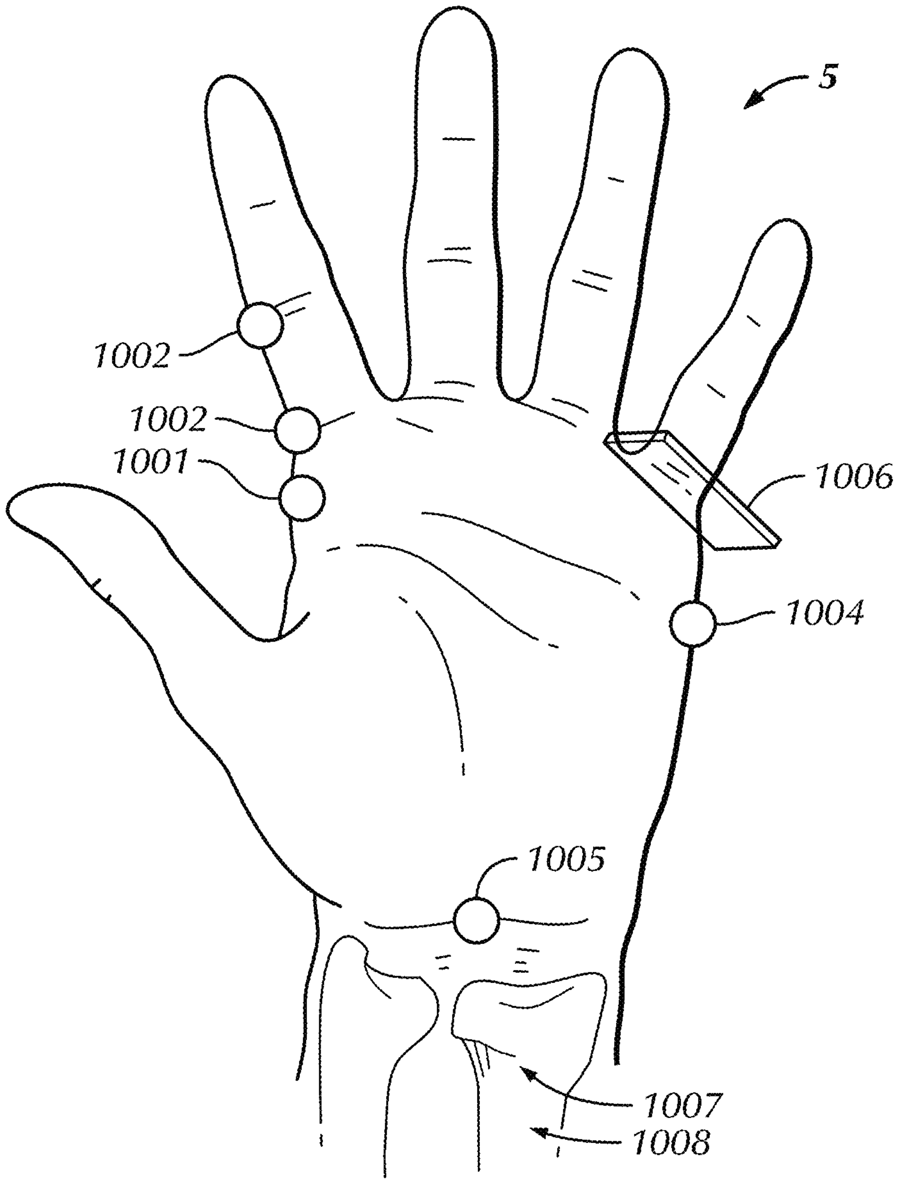
FIG. 10 represents an exemplary embodiment of a shape of a patient's hand with target features predicated, bones, cutting lines, X-RAY image features which are all predicted by artificial intelligence that may be utilized with the 3D scanner of FIG. 1.

Referring to FIG. 10, as a non-limiting example utilizing the preferred scanner 10, hand features are detected by the preferred scanner 10 in a preferred hand scanning technique, which is trained by the prescribed CNN network. The OpenCV and datasets of COCO Keypoints challenge, MPII Human Pose Dataset, VGG Pose Dataset, and local datasets are collected to train the network for feature detection with the CNN network. The detection can be performed with any other computational intelligence techniques to predict the features from a 3D/2D digital file, such that the preferred scanner 10 is not limited to the specific techniques, methods and systems described herein.

The present identified hand features 1001, 1002, 1003, 1004, 1005, 1006, 1007, 1008 are hand keypoint features collected utilizing the scanner 10 and directed by the central processor 503. Confidence and affinity maps are preferably parsed by greedy inference to produce the 2D keypoints for a majority of patients in the image or digital file as 3D keypoint within following preferred codes:

```
    # input image dimensions for the network
    inHeight = 368
    in Width = int(((aspect_ratio*inHeight)*8)//8)
    inpBlob = cv2.dnn.blobFromImage(frame, 1.0 / 255, (inWidth,
inHeight), (0, 0, 0), swapRB=False, crop=False)
    net.setInput(inpBlob)
    output = net.forward( )
```

Detected preferred keypoints of the hand assist the scanner 10 to make the probable cutting lines for the 3D cast splint, brace, and related medical devices that may be constructed utilizing the model of scanned digital file. The probability of points preferably draws the cutting lines for the 3D scanned file. The cutting lines and keypoints usage (short cast, the specific splint, cast, brace or other medical device) are prescribed, preferably before the scanning process begins. An interactive module is preferably applied to the scanner machine 10 that helps the customer to modify the key points which are not in the correct position. In this case, the scanner machine 10 learns how the customer corrects the key points to improve its probability function and update its weight to gain better accuracy in the final digital file and mapping features.

for i in range (self.nPoints):

```
    # confidence map of the corresponding body's part.
    probMap = output[0, i, :, :]
    probMap = cv2.resize(probMap, (frameWidth, frameHeight))
    # Find global maxima of the probMap.
    min Val, prob, minLoc, point = cv2.minMaxLoc(probMap)
    if prob > threshold :
    cv2.circle(frame, (int(point[0]), int(point[1])), 2, (0, 0,
int(255*prob)), thickness =- 1, lineType=cv2.FILLED)
  cv2.putText(frame, "{ }".format(self.rearrange_finger_indices[i]),
(int(point[0]), int(point[1])), cv2.FONT_HERSHEY_SIMPLEX, 0.1,
(0, 0, 255), 1, lineType=cv2.LINE_AA)
    # Add the point to the list if the probability is greater than the
threshold
    points.append(np.array([int(point[0]), int(point[1]),prob]))
    # points_probs.append(prob)
  else :
    # points_probs.append(0)
    points.append(np.array([0, 0,0])
```

Referring to FIG. 10, keypoints proximate the distal end of the ulna 1007, 1008 may be comprised of features of the X-ray shown for the fractures and dislocated bones and also the 3D scan file. This keypoint identification of the ulna 1007, 1008 assists the scanner machine 10 to locate the deformation, dislocation and related features for further decision making, parametrization as engravements, pressure configuration, thickness, lock insertion, and related decisions.

Following a traumatic event or other event resulting in orthopedic damage or injury, swelling may occur to the body part, such as the hand 5, making scanning with the 3D machine or scanner 10 and creation of a printed case or splint difficult and inaccurate. Where the physician, technician or 3D machine or scanner 10 detects significant swelling of the body part 5 that may impact the accuracy of the digitized base cast or splint, the opposing or contralateral body part may be scanned using the 3D machine or scanner 10 and the digitized base cast may be electrically manipulated to create a mirror image of the digitized base cast for application to the impacted body part once the swelling dissipates. The collected data may be manipulated by the processing unit 503 to create the 3D splint or cast of the contralateral body part and the processing unit 503 is then able to create the mirror image of the 3D splint or cast by manipulating the collected data. In addition, the processing unit 503 may identify swelling or injury based on the collected data and define a bone stimulation port between proximal and distal ends of shell portions of the 3D splint or cast. In addition, the technician or physician operating the 3D machine or scanner 10 may place marking tape on the patient's body part at a location for venting holes, a logo, interfacing edges of the 3D splint or cast, locations for flex areas, locations for first or second engagement mechanisms, locations for reinforcement portions, locations for stimulation ports, locations for added padding or coatings over prominences or areas of concern or injury, markings for a targeted pathology or treatment zone and other features of the 3D splint or cast. The 3D splint or cast may further be designed as an initial version with additional space to accommodate the swelling and a final version for application when the swelling subsides, as well as a plurality of intermediate versions for application at different stages of swelling or deformation.

The base cast 1018 constructed by the 3D machine or scanner 10 may include the bone stimulation port formed on one or both shell portions of the splint or cast. The bone stimulation port is formed during the 3D printing process with the 3D machine or scanner 10 and is configured to receive a bone stimulator for treatment of the patient's body part. The bone stimulation port may be comprised of two bone stimulation ports with one positioned on a front portion of the splint or cast and one positioned on a back portion of the splint or cast. The bone stimulation ports may be positioned near the wrist of the patient in the mounted configuration and may be otherwise positioned or arranged based on the patient's condition or physician requirements. The bone stimulation port may also be defined on the first shell portion proximate the base of the metacarpal of the thumb in the mounted configuration. The cast or splint may be configured to treat scaphoid fractures, carpal bone fractures and conditions related to the radial styloid. When utilized as a splint, the first shell portion 1018 may be secured or mounted to the patient's arm with straps by itself to substantially immobilize the thumb. In addition, the bone stimulation port may be otherwise positioned on the first or second shell portions to promote healing or otherwise stimulate bones or other tissue. The bone stimulation port may alternatively be positioned over the fourth and fifth metacarpals on the first and/or second shell portions of the 3D splint or case for application of bone stimulation. The bone stimulation port may alternatively be positioned proximate the second and third metacarpals in the mounted configuration on the first and second shell portions, but are not so limited and the base cast may include only a single bone stimulation port on one of the first and second shell portions or may be constructed without the bone stimulation port, without significantly impacting the design and construction of the preferred cast or splint produced by the 3D machine or scanner 10. The 3D cast or splint 1018 is not limited to inclusion of the bone stimulation port or to the location of the bone stimulation ports described herein. The preferred cast or splint 1018 may be constructed without the bone stimulation port and may be configured having the bone stimulation port in nearly any location on the first and second shell portions splint or cast. The bone stimulation port is preferably sized and configured for receipt of a physician preferred bone stimulator. The cast or splint 1018 and the 3D printing process for constructing the cast or splint 1018 is particularly adaptable for positioning the bone stimulation port at nearly any location on the cast or splint 1018. The bone stimulation port is preferably integrated into the digitized base cast by the designer and printed into one or both of the second shell portions of the splint or cast 1018. Accordingly, the bone stimulation port can be moved to various locations and quickly produced with the 3D machine or scanner 10.

The 3D machine or scanner 10 may also be designed and configured such that the acquired data is utilized by the processing unit 503 to construct a splint or cast 1018 having a relatively stiff and strong base material and a relatively flexible coating on the external surfaces of the base material. The cast or splint 1018 preferably includes a first shell portion and a second shell portion that comprises the base cast or splint 1018. The first and second shell portions preferably include the coating applied to the external surfaces. The base cast 1018 is not limited to including the coating and the base cast or splint may be mounted to the patient's body part to immobilize or limit motion to a joint in a mounted configuration. The coating may alternatively only be applied to surfaces of the base cast or splint 1018 facing the patient's skin for additional protection of the skin to limit irritation or treatment of wounds. The coating may be constructed of a breathable material. The coating is preferably comprised of an inert polymeric material, such as silicone, which has preferred properties for direct contact with the patient's skin, particularly when placed on scars to promote skin healing. The coating is not limited to silicone coatings and may be comprised of any material that may be adhered to the first and second shell portions, withstand the normal operating conditions of the cast or splint 1018 and is able to take on the size and shape of the preferred coating. In addition, the inert polymeric coating is preferably flexible to accommodate changes to the patient's anatomy, such as swelling or reduction of swelling to maintain the relative form and custom fit around and on the patient's body part for a limited period of time after application of the cast to the body part, such as at least six to eight (6-8) weeks. The coating is also not limited to inert polymeric materials or to specifically polymeric materials. The coating may be comprised of nearly any material applied to the base cast 1018 in nearly any manner that is able to take on the general size and shape of the coating, withstand the normal operating conditions of the coating and perform the described, preferred functions of the coating. For example, the coating may be comprised of a non-polymeric material that is applied to the base cast 1018 to promote healing of a body part to which the cast or splint 1018 is applied. In addition, the cast or splint 1018 may be constructed and deployed as only the base cast without the coating, such as for temporary immobilization while the patient is assessed or temporarily immobilized for subsequent treatment.

The 3D machine or scanner 10 of the first preferred embodiment is able to fabricate a splint or cast 1018 with a custom fit, breathability, and durability with affordable materials. The scanning of the patient's anatomy may be collected by the patient themselves, such as by utilizing their own camera or cameras 101, 102, 103, 104 and transmitting the acquired data to the processing unit or central server 503. This remote scanning by the patient or a caregiver promotes social distancing and provides additional convenience for the patient, caregiver and physician. The patient or caregiver may collect videos and/or photographs and transmit the data to the processing unit or central server 503. The processing unit or central server 503 processes the collected data to define the digital splint or cast and the digital splint or cast is transmitted to a 3D scanner for manufacture of the 3D splint or cast 1018. The manufactured 3D splint or cast 1018 is then delivered to the patient or the patient visits the physician for final fitting and application to the patient. The splint or cast 1018 may be updated by relatively quick reprocessing by the processing unit or central server 503 and the 3D printer or scanner.

Figure 11:
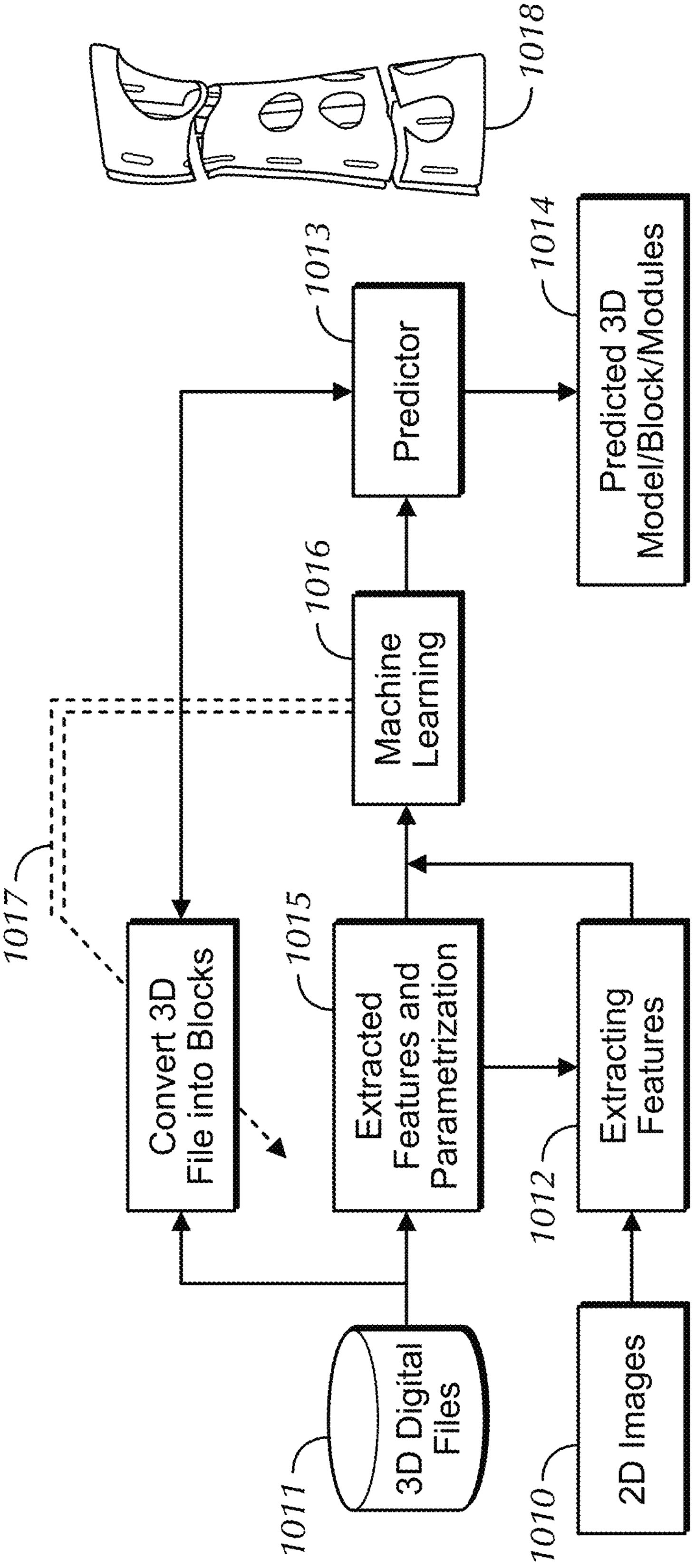
FIG. 11 represented a flowchart that generates a 3D model from the minimum number of 2D images within the trained 3D digital files and a side elevational view of a cast or splint that may be produced from the 3D scanner of FIG. 1.
Figure 12:
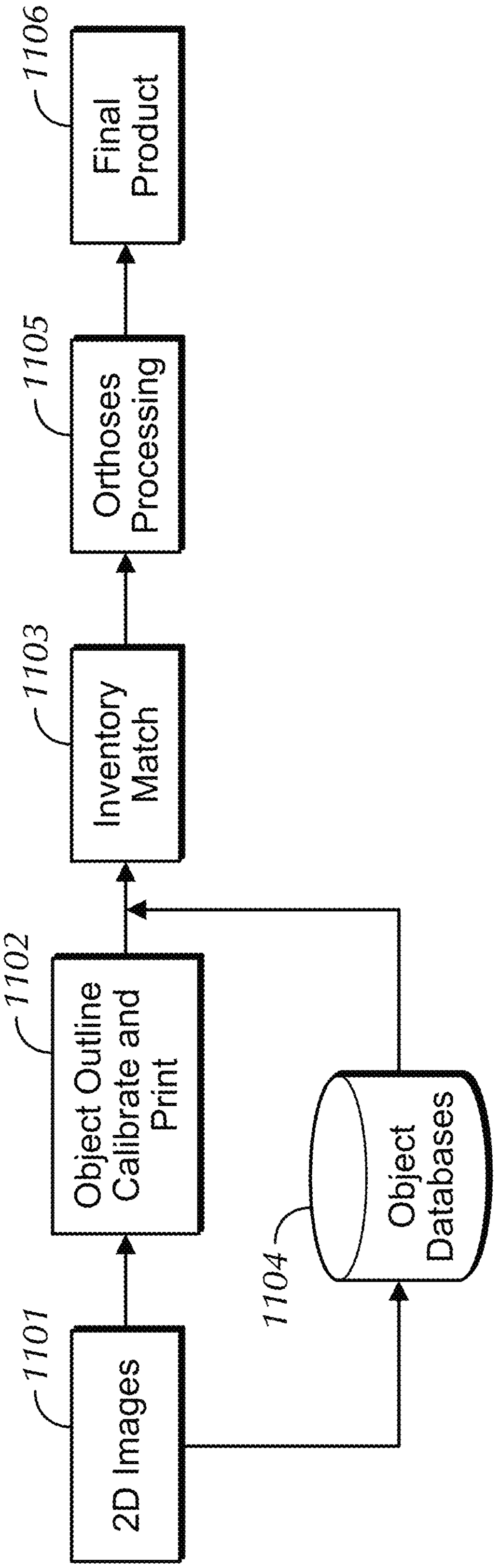
FIG. 12 is a block diagram representation of a process for creating a 3D cast or splint from 2D images of a patient's anatomy utilizing the 3D scanner of FIG. 1.

Referring to FIG. 11, a dataset of 3D digital files 1011 is used as an input for training a machine learning module 1016 of the 3D machine or scanner 10. The machine learning module 1016 may be positioned within or be a part of the processing unit or central server 503. Geometrical and clinical features, as explained herein, see specifically FIG. 10, are extracted with an image processing module 1015 and are sent to the machine learning module 1016. Geometrical features can be a diameter of the patient's wrist, length of the thumb, and clinical data is the place of swelling, fractures, wounds, and other clinician or patient determined marks etc. The preferred 3D machine 10 is trained based on unsupervised learning and optimized by a hyperparameter optimization to classify/cluster the extracted features into multiple sizes and/or a fully customized shape. This will not limit the 3D machine 10 to unsupervised learning and the 3D machine 10 may utilize an alternative AI training algorithm that can cluster or classify the input data for manipulation and manufacture, preferably by 3D printing, of a 3D splint or cast 1018.

New input 2D images 1010, which are preferably calibrated by the measurement unit (such as physical or radiographic marker, calibration background or other sizer), may also be used as an input to generate the cast, splint or brace 1018 based on the extracted features. These input 2D images 1010 can be from a mobile device camera with the assistance of an app (on multiple platforms), cloud based web upload or other acquisition platforms housed on Health Insurance Portability and Accountability Act ("HIPAA") compliant routing and servers. Significant features are preferably identified with a pre-knowledge of expert, machine hyper optimization, etc. The preferred 3D machine 10 generates the 3D casts, splint, brace, or other digital models 1018 based on the trained features as FIG. 10 or other clinical identifiers. The 3D digital file, which is preferably stored in the central server 503 is segmented into multiple parts based on the variation on extracted features as circumferences, curvatures, and straight-line or key points explained in FIG. 10. Based on the minimal energy strategy and entropy of the machine learning theory in this preferred system, the number of blocks, features, and other parameterized identifiers are optimized. The number of output blocks can be varied based on the body part; therefore, the algorithm parametrizes the number of sizes for each block of the cast or splint 1018 and preferably generates the optimized number of sizes based on the input and trained features. The following algorithm is part of the hyper parametrization for the size of casts 1018 to find the most optimal number for sizing of the cast, brace and splint 1018 (such as 16 preferred sizes):

```
for i in range(1, 16) :
#    kmeans = KMeans(n_clusters=i, init= 'k-means++',
max_iter=300, n_init=15, random_state=0)
#    kmeans.fit(X)
```

With the most common sizes of the parts premanufactured, some pre-fabricated parts may be substituted by the machine learning environment to complement the custom generated parts. The algorithm may route the production of the orthoses based on temporal, inventory and geographic optimization. Scanned data can feed directly into the electronic medical record of the patient for automatic documentation and reproducibility of the orthosis allowing faster turnaround and improving the ease of modification.

Referring to FIGS. 1-11, in a preferred process, an algorithm in the processing unit or central server or processor 503 can correlate an appropriate size of the orthoses for the scanned patient within the 2D or 3D images (digital photo, capture, radiograph, or 3D scan or advanced medical imaging) captured using the 3D machine or scanner 10 or an alternative imager or camera. In a preferred method, a patient takes 2D images (or uploads medical imaging or 3D images, potentially from the 3D machine or scanner 10), and the algorithm calibrates with or without manual input the required measurements for fitting the orthoses, cast, splint or brace to the patient and the patient's body part, such as wrist circumference, forearm length, leg length, ankle size and shape, knee size and shape and related dimensions for the best fit model to create the preferred orthoses. The best fit model for the orthoses is communicated by the processing unit or the central server 503 with the 3D machine or scanner 10 to recommend the most appropriate fit and type of orthosis (sizes and type of prefabricated splint/brace/cast) for the patient and their particular injury. The cast/splint/brace sizes were given to the algorithm based on the product catalog, expert knowledge, and machine learning of the most appropriate fit and related information for the patient. A neural network classification described herein can predict the output size based on calibrated 2D images with high accuracy.

A preferred process flow includes: 1. providing splint/brace/cast sizes to the 3D machine 10 based on product catalog, inventory, expert knowledge, or prior data (AI—machine learning); 2. 2D images are preferably acquired by the patient or point of the service provider, and are sent to the processing unit or central server 503 with an application or online web app., (alternatively, compatible image data in the form of digital radiograph, advanced medical imaging [i.e. CT/MRI], 3D scan, and related information can be input); 3. the algorithm or human measures required distances (based on product catalog, expert knowledge, machine learning database); 4. measured distances are provided to the algorithm and compared/integrated into a virtual model or required sizing input; 5. the algorithm of the processing unit or central server 503 recommends the most proper size for the type of orthosis; 6. the most proper size is selected at the distribution point to give, courier, or deliver to the patient or the point of the service location for application to the patient; 7. custom tracking and feedback is provided throughout the process to the prescriber, patient, and distributor; 8. Inventory optimization may be included for proper routing of the device; 9. remote evaluation of re-uploaded images with the orthosis may be checked for appropriate fit based on the above process, fit, deviation from virtual model or via manual evaluation (orthotist/provider checks fit) by providing 2D or 3D scanned images to the processing unit or central server 503.

The preferred embodiments of the present invention utilizes 3D to 2D projection techniques to generate orthoses, such as braces, splints, neck collars, boots, knee immobilizers, and related orthoses. In order to predict and generate the 3D digital file of individual 2D images, the following flow of steps are preferably followed: 1. The trained machine 10 picks the most fitted limb by classification and follows a regression to make a decision between proper choices with the smallest error (this can be performed by iterative loops to find the matched keypoints with solving a minimization problem); 2. the preferred algorithm of the processing unit or central server 503 calculates minimization error in two loops of scaling factor and database limbs models, such as hands; 3. the algorithm picks the best choices of 3D files in the database and by a decision-making algorithm matches the most proper one between recommended scaling factor and model from the database; 4. project the database model in three planes of (X, Y), (X, Z), and (Y, Z); 5. use the founded scaling factor to scale the database model into three planes; and 6. reconstruct the 3D model by three planes which are a scaled model of the model at step 3.

The preferred process is also augmented by using scanning, such as with the 3D machine or scanner 10, or 2D image acquisition, such as with a smartphone, tablet or other image capture device. The 2D images may be calibrated by utilizing a reference mark or object positioned near the patient's body part and collecting a series of images of the body part and the reference mark or object to facilitate sizing of the implant by the processing unit or central server 503. The reference mark may be comprised of a scale, ruler, mark on the patient's body part having a predetermined size and shape, a coin having a predetermined size or shape, such as a quarter, multiple reference marks or objects, an immobilizing or reference device that is attached or secured to the patient's body part or other marks, objects or devices that may be positioned on, adjacent or in proximity to the patient's body part that facilitate scaling of the 3D model created by the processing unit or central server 503 and construction of the 3D orthoses based on the images and data acquired by the preferred system. The patient may take multiple images of their forearm that requires a brace, splint, cast or implant with reference marks, a reference object or a brace having a predetermined size and shape attached, adjacent to or in proximity to the forearm that the processing unit or central server 503 utilizes to size the 3D model and related 3D orthoses that is created from the acquired data. The processing unit or central server 503 is preferably able to size and "fit" the 3D orthosis based on the images collected with the reference marking or object therein. As a non-limiting example, the processing unit or central server 503 may utilize this preferred method with a patient taking a picture of their hand with a quarter on or adjacent to the hand and the algorithm of the processing unit or central server 503 is able to calibrate a size and shape for a wrist brace required for the patient's wrist, such as a stock "XL wrist brace," "M wrist brace," "S wrist brace" or other sized or shaped wrist brace that is in inventory at the care provider.

Referring to FIGS. 1, 5 and 10-12, the preferred embodiments of the present invention utilizes 2D to 3D projection techniques to generate 3D printed or constructed orthoses, such as braces, splints, neck collars, boots, knee immobilizers, and related orthoses with thermoplastics and molding techniques.

In a preferred process or method, 2D images 1101 are processed through or received by the central server 503 (See FIG. 11). As described above, particularly with respect to FIGS. 11 and 12, 2D images are processed in an object outline calibrate and print 1102 step to generate the 3D model of the limb or any impacted body part with Machine learning and Image processing techniques to estimate parameters for the 3D model and construct the final limb 3D splint or cast 1018, based on information from the object database 1104. The object outline calibrate and print 1102 step may utilize object databases 1104 to develop the 3D model. Through an edge detection algorithm, the outline of the 2D images of the limb or other body part are extracted. The outline is printed on a sheet to define a preliminary splint or cast for further cuts and usages.

An inventory match 1103 following the print includes the outline of the 2D Image and also the generated 3D model of the limb. The inventory for the inventory match 1103 may include a plurality of standard or relatively frequently used 3D base models (for example fifty (50) sizes). The algorithm decision making based on the previous 2D/3D projection and parameter estimation selects one of the standard or relatively frequently used 3D base models or sizes, which has the minimum error compared to the captured 2D Images, based on the described decision making. The selected standard or relatively frequently used 3D base model is picked for further orthoses processing 1105. Orthoses processing 1105 is varied based on the material that will be utilized for the 3D model. As a non-limiting example, a selected standard or relatively frequently used 3D base model constructed of a thermoplastic material may be cut, machined, subtracted or otherwise manipulated by other manufacturing techniques from the printed sheet outline and molded onto the generated 3D model, which is printed previously or taken out of the inventory with the known size. The 3D model may contain a heating filament to simplify the molding process or the process may be otherwise automated. The inventory match 1103 may include the process of the central server 503 selecting one of a variety of differently sized 3D base models from an inventory of 3D base models and subsequently printing additional material onto the 3D base model or removing material from the 3D base model to develop the final product or final 3D cast, splint or brace 1018, which is preferably produced as the 3D final product 1106.

As part of the orthoses processing 1105 step, a strengthening rib or reinforcement portion along an axis to limit or prevent predetermined movements of the limb or other body part to promote healing. The orthoses processing 1105 step may also include manipulating the material of the 3D base model to define a flex area in the 3D base model to facilitate flexing of the limb or other body part, which may also promote healing of the body part. The orthoses processing 1105 step may further include opening or expanding venting holes in the 3D base model at predetermined areas to provide for visual inspection of the patient's limb, skin or for other clinical purposes to that a medical professional may visually inspect healing, apply medication, gain access for bone stimulation or other therapies. The orthoses processing 1105 step may also include adding additional material to the 3D base model to reduce the size of the venting holes to protect the patient's skin, generally stiffen the 3D base model or otherwise manipulate the properties of the final 3D case, splint or brace 1018 based on the patient's specific injury and requirements.

Referring to FIGS. 4, 5, 7A, 7B and 9-14, a second preferred 3D scanner or machine, generally designated 1200, and the described actuation mechanism that may be utilized with the scanner 1200, is an exemplary description and not meant to be limiting. The second preferred 3D scanner or machine 1200 may include nearly any actuation mechanism with a different type of control mechanism, processing units, motors, mechanical elements and other features that facilitate performance of the preferred functions, operation in the normal operating conditions of the second preferred scanner 1200 and functioning within the preferred size and shape of the scanner 1200. The interface between components of the second preferred scanner 1200 that communicate with each other to support operation of the scanner 1200 can be in a cable, wireless, Bluetooth, or any similar technologies. In addition, the second preferred 3D scanner system 1200 operates based on the methods, processes and with the features of the first preferred 3D scanner system 10, such as by incorporating and utilizing the first preferred cameras 101, 102, 103, 104 and lasers 105, 106, 107, the operation and method described with FIGS. 4 and 5, the operation and methods described with FIGS. 7A and 7B, the methods and optimization described with FIG. 9, the methods, capture techniques and machine learning described with FIGS. 10-12 and any of the above features and methods of the first preferred embodiment that may be utilized with the scanner system 1200 of the second preferred embodiment, as would be apparent to one having ordinary skill in the art based on a review of the present disclosure.

Figure 13:
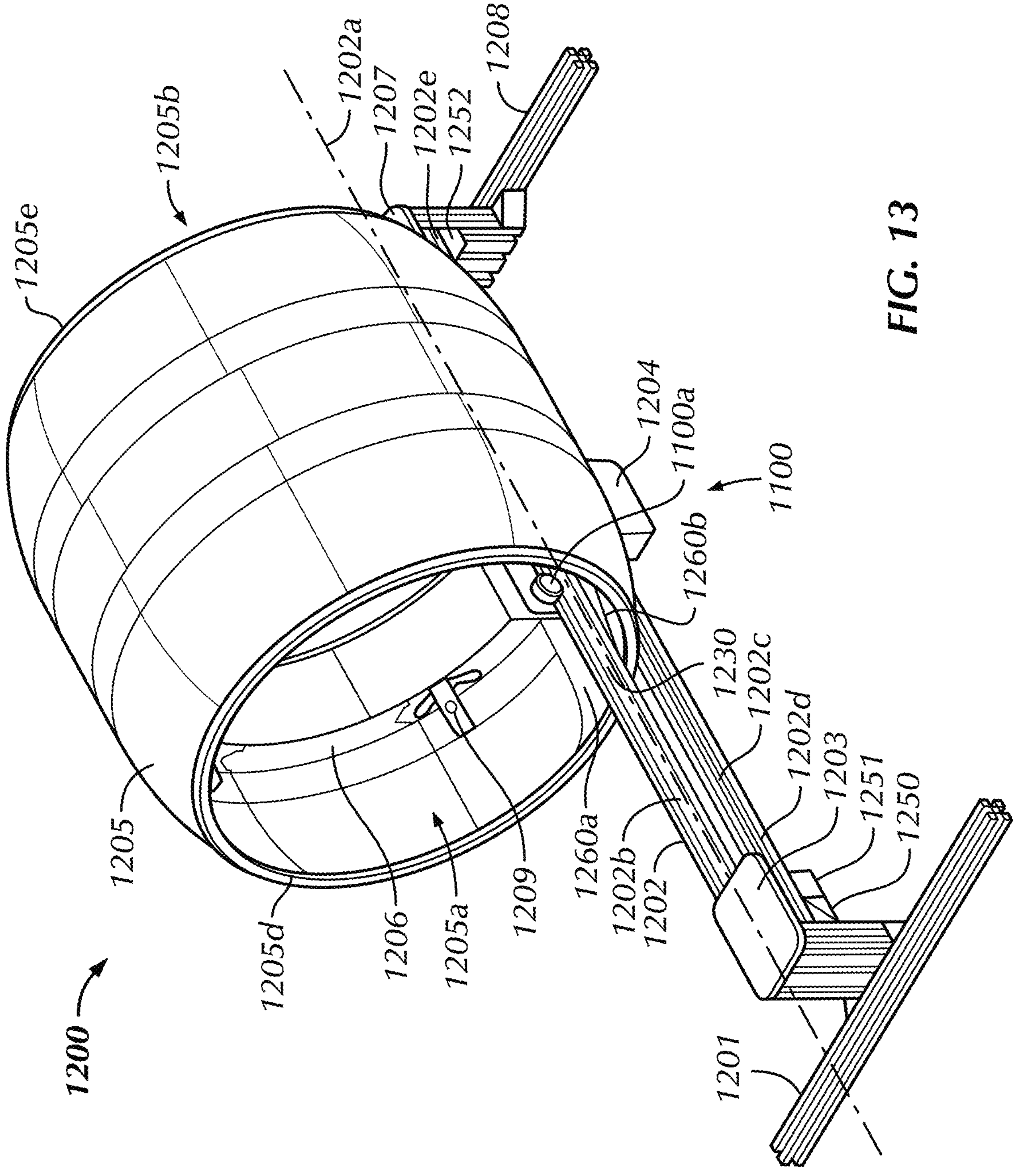
FIG. 13 is side perspective view of a 3D scanner in accordance with a second preferred embodiment of the present invention.
Figure 14:
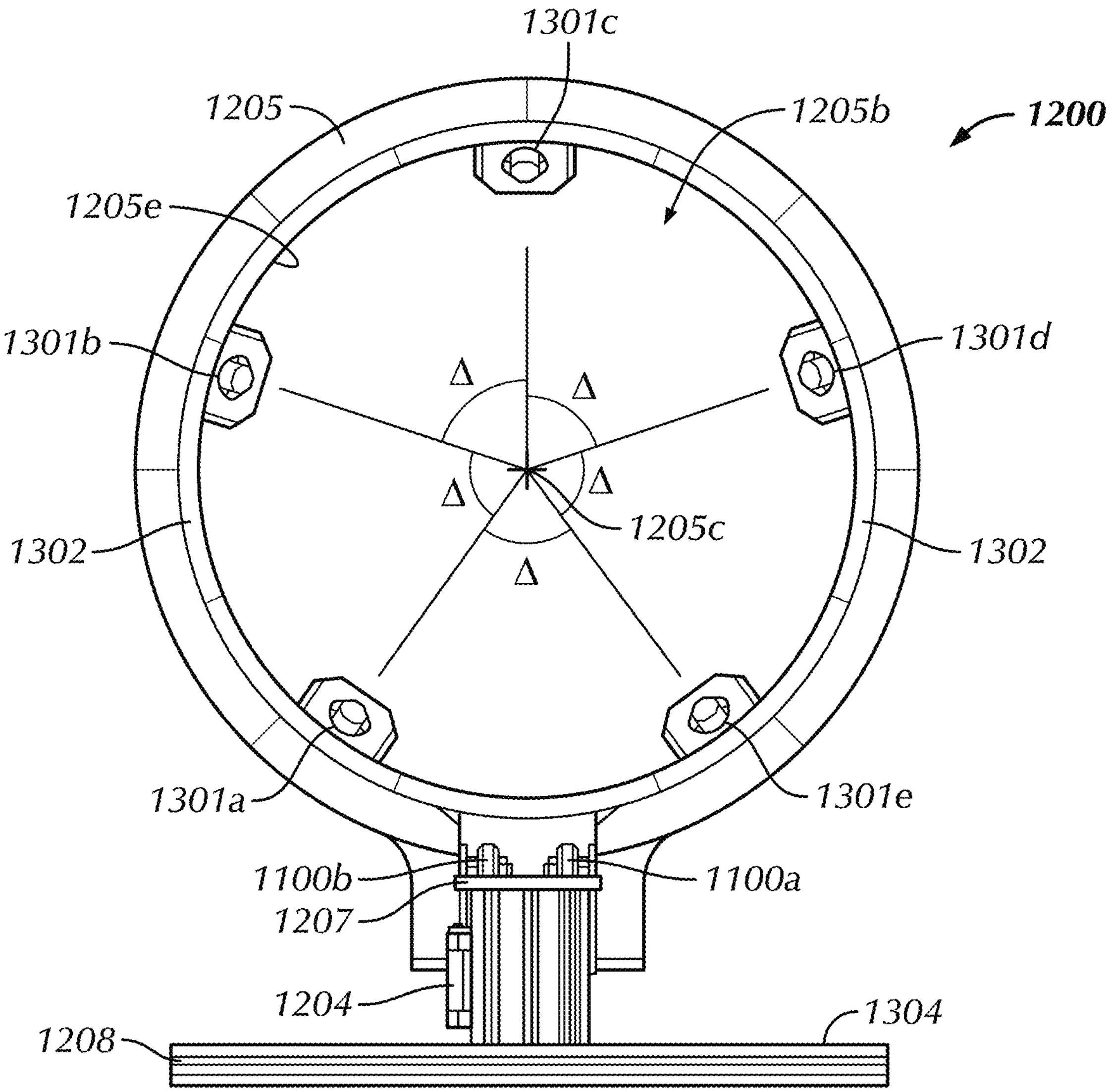
FIG. 14 is a front elevational view of the 3D scanner of FIG. 13.

Referring to FIGS. 13 and 14, a second preferred embodiment of a 3D scanner or machine 1200 is preferably used for capturing a 3D model of an object, such as a patient's limb. The second preferred 3D scanner 1200 operates such that the scanning process doesn't require a dark environment and can be used in both light and dark environments. The 3D scanner 1200 of the second preferred embodiment transmits and processes the data from cameras 1301 and lasers 1209 similar to or substantially the same as the first preferred scanner system 10 and the creation of 3D model and the 3D printing of the cast or splint may be utilized with any of the techniques described in the first preferred embodiment in the second preferred 3D scanner system 1200.

In the second preferred 3D scanner 1200, a tube 1205 is mounted to and moves on a rail 1202 in either left-to-right or front-to-rear direction along a travel axis 1202*a* of the rail 1202. In both directions, the second preferred 3D scanner 1200 can capture video and/or still/2D images and convert the video, scan and/or still/2D images into a 3D digital file, similar to the techniques described above with respect to the first preferred 3D scanner 10. The 3D scanner 1200 includes microswitches 1251, 1252 mounted on or near endplates 1203, 1207 that are connected to the rail 1202. The microswitches 1251, 1252 include a first microswitch 1251 mounted to a first endplate 1203 and a second microswitch 1252 mounted to a second endplate 1207. The first endplate 1203 is preferably connected to a first rail end 1202*d* of the rail 1202 and the second endplate 1207 is preferably connected to a second rail end 1202*e* of the rail 1202. The first and second microswitches 1251, 1252 are preferably mounted under the first and second endplates 1203, 1207 and detect proximity of the tube 1205 during use. The preferred tube 1205 includes end stops that interact with the microswitches 1251, 1252 to control the movement of the tube 1205 at the ends of the rail 1202 proximate the first and second endplates 1203, 1207. The tube 1205 is preferably driven in its movement by an actuation mechanism that includes a motor 1250. In the second preferred embodiment, the motor 1250 is mounted to the first endplate 1203, although such mounting is not so limited and the motor 1250 may be otherwise mounted, such as to the second endplate 1207 or to the rail 1220. The actuation mechanism also preferably includes encoders configured to move the tube 1205 along the rail 1202, mechanical elements including a belt, ball bearings, a roller bearing, position sensors and coupling components or elements to attach the belt to the tube 1205.

The computer 501, the processor 503 or the user can control the position of tube 1205 on the rail 1202, as well as the movement of the tube 1205 along the rail 1202 for capturing the video and images of the object during operation. Scanner holders or legs 1201, 1208 are used to stabilize the 3D scanner 1200 and may be adjusted in height with a screw or a hydraulic mechanical system to raise or lower the tube 1205 to adapt to the positioning or comfort of the patient, the object or the body part being scanned.

The laser 1209 of the second preferred embodiment provides a stripe of light to illuminate the object that is positioned in the tube 1205 for scanning. The laser 1209 is preferably comprised of five (5) lasers 1209 that are mounted inside the tube 1205. The lasers 1209 are mounted inside the tube 1205 on a laser holder 1206 that is comprised of a shelf or rib that extends generally around the inside of the tube 1205 in a frusta-circular configuration. The laser holder 1206 is configured to provide strength and stiffness to the tube 1205 and to facilitate mounting of the lasers 1209 to the tube 1205. The laser 1209 is not limited to being comprised of five (5) lasers 1209 mounted to the inside of the tube 1205 and may be comprised of nearly any number of lasers 1209 that are able to perform the preferred functions and withstand the normal operating conditions of the preferred laser 1209 of the second preferred embodiment.

The camera 1301 is configured to capture 2D images of the object that is positioned in the tube 1205 during operation. The camera 1301 is preferably comprised of five (5) cameras 1301 mounted inside the tube 1205. The cameras 1301 are preferably mounted to the tube 1205 on a camera mount 1302 that is comprised of a frusta-circular structural element that provides strength and stiffness to the tube 1205 and stable mounting locations for the cameras 1301. The camera 1301 is not limited to being comprised of five (5) cameras 1301 mounted to the inside of the tube 1205 and may be comprised of nearly any number of cameras 1301 that are able to perform the preferred functions and withstand the normal operating conditions of the preferred camera 1301. The preferred five (5) cameras 1301 are generally evenly spaced from each other inside the tube 1205 and mounted on the camera mount 1302. The preferred five (5) cameras 1301 include a first camera 1301*a*, a second camera 1301*b*, a third camera 1301*c*, a fourth camera 1301*d* and a fifth camera 1301*c*. The first and second cameras 1301*a*, 1301*b* preferably define a camera spacing angle Δ measured relative to a tube central axis 1205*c*. The camera spacing angle Δ is approximately seventy-two degrees (72°) and each of the adjacent cameras 1301 are also spaced from each other at the spacing angle A but are not so limited. The cameras 1301*a*, 1301*b*, 1301*c*, 1301*d*, 1301*e* may be spaced and arranged in nearly any manner that facilitates collecting the images of the object inside the tube 1205 during operation.

The tube 1205 is configured to move generally along the travel axis 1202*a* of the rail 1202 from left-to-right and/or front-to-rear between the ends of the rail 1202. The tube 1205 includes a first tube end 1205*a* and a second tube end 1205*b* that are open such that the object may be positioned in the tube 1205 during the scanning process. The camera 1301 and the laser 1209 are mounted inside the tube 1205 between the first tube end 1205*a* and the second tube end 1205*b*. The rail 1205 of the second preferred embodiment includes a first track 1202*b* and a second track 1202*c* that are substantially grooves in the rail 1205 that extend along the length of the rail 1205 substantially parallel to the travel axis 1202*a*, although are not so limited and may extend along only portions of the rail 1202 or the rail 1202 may be otherwise designed and configured to facilitate movement of the tube 1205 along the rail 1202. A first wheel 1100*a* is preferably mounted to a first longitudinal stiffening rib 1260*a* and is positioned in the first track 1202*b* and a second wheel 1100*b* is preferably mounted to a second longitudinal stiffening rib 1260*b* and is positioned in the second track 1202*c* in the assembled configuration. The first and second tracks 1202*b*, 1202*c* guide the movement of the tube 1205 as the wheels 1100*a*, 1100*b* roll along the tracks 1202*b*, 1202*c* and movement of the tube 1205 along the rail 1202 along the travel axis 1202*a*. The second preferred 3D scanner is not limited to including the first and second wheels 1100*a*, 1100*b* or the first and second tracks 1202*b*, 1202*c* and may be otherwise designed and configured to facilitate movement of the tube 1205 along the rail 1202, such as a pin and track, opposing sliding surfaces or other arrangements that direct and guide the tube 1205 along the rail 1202.

The second preferred tube 1205 includes a first continuous ring 1205*d* at the first tube end 1205*a* and a second continuous ring 1205*e* at the second tube end 1205*b*. The first and second continuous rings 1205*d*, 1205*e* provide structural support for the tube 1205 and are preferably constructed of a relatively stiff, structural material. The tube 1205 also includes a channel 1230 extending through the tube 1205 between the first ring 1205*d* and the second ring 1205*e* positioned adjacent the rail 1202 in the assembled configuration. The channel 1230 accommodates the rail 1202 and connection of the first and second longitudinal stiffening ribs 1260*a*, 1260*b* to the wheels 1100*a*, 1100*b* and a belt that drives the tube 1205, as is described in greater detail below. The first stiffening rib 1260*a* extends along a first side of the channel 1230 between the first tube end 1205*a* and the second tube end 1205*b* and the second longitudinal stiffening rib 1260*b* extends along a second side of the channel 1230 between the first and second tube ends 1205*a*, 1205*b*.

In the second preferred embodiment, the rail 1202 and the tube 1205 are supported off of a floor surface by a first leg 1201 and a second leg 1208 that are connected to the rail 1202. The first and second legs 1201, 1208 are preferably constructed of a relatively stiff, structural material that is able to take on the general size and shape of the first and second legs 1201, 1208, withstand the normal operating conditions of the first and second legs 1201, 1208 and perform the preferred functions of the first and second legs 1201, 1208, as are described herein. The first and second legs 1201, 1208 may be constructed of a polymeric or metallic material, such as polyvinyl chloride, aluminum or steel. The first and second legs 1201, 1208 may also be configured to raise and lower the rail 1202 and tube 1205 relative to the support surface or floor, manually or automatically, to arrange the tube 1205 for easy insertion of the object for scanning.

The 3D scanner 1200 is utilized with dual scanning such that the lasers 1209 and/or cameras 1301 in the tube 1205 operate in a double or two scan process, including left-to-right and front-to-rear scanning as the tube 1205 travels along the rail 1202. This process is used to scan the object, then used to scan the texture and placed features or landmarks on the object with the installed cameras (monochrome, DSLR, Infrared, and etc.) 1301 and/or lasers 1209 during the second phase of the scanning process. In the preferred embodiment, the lasers 1209 are utilized to scan the object to create the 3D model of the object in a first pass along the rail 1202 and the cameras 1301 are subsequently utilized to identify or scan the texture and placed features or landmarks on the object during a second pass along the rail 1202. The preferred lasers 1209 may be comprised of infrared, near-infrared, red, green, and other specific wavelengths/bandwidth types of lasers. The preferred lasers 1209 with equipped specific lens are mounted on the laser holders 1206 that secure the lasers 1209 to the tube 1205 and result in the lasers 1209 moving with tube 1205 during operation.

The preferred 3D scanner 1200 also includes the cameras 1301 positioned on a camera mount 1302 inside the tube 1205. The cameras 1301 are preferably fixed to tube 1205 and move with the tube 1205 and lasers 1209 on the rail 1202 during operation. In the preferred second embodiment, a securing block 1204 is secured or connected to the tube 1205 proximate the rail 1202, preferably below the rail 1202, to secure the tube 1205 to the rail 1202 on a transport mechanism 1100*a*, 1100*b* to movably connect the tube 1205 to the rail 1202. In the second preferred embodiment, the transport mechanism is comprised of wheels 1100*a*, 1100*b* that facilitate movement of the tube 1205 along the rail 1202 during operation. The wheels 1100*a*, 1100*b* may be directly driven to move the tube 1205 or may be passive and facilitate the translation movement of the tube 1205 that is pulled along the travel axis 1202*a* by a belt or a chain (not shown) connected to the securing block 1204 or the tube 1205. The movement of the tube 1205 is preferably controlled and driven by the computer 501 and/or the central processor 503. In order to fix or secure the object, preferably the patient's limb, relative to the tube 1205 and rail 1202, a holder(s) (not shown) can be installed on the rail 1202, the endplates 1203, 1207, the scanner holders or legs 1201, 1208 or to an external support adjacent to the 3D scanner 1200. The holder preferably secures or fixes the body limb or scanning object in the scanning area above the rail 1202 for image capture and creation of the 3D model of the object, preferably the limb. The size of the scanning area can be modified by changing the size of the tube 1205, the length of the rail 1202 or making other adjustments to the 3D scanner 1200.

The angle and number of the cameras 1301 can be changed to a higher or lower number to maintain a scanning area without any blind spots based on the object's complexity and shape. The process to develop and construct a 3D digital file of the scanned object is preferably the same as the description above with respect to the first and second preferred embodiment although not limiting and various processes may be utilized to develop the 3D model of the scanned object utilizing the 3D scanner 1200 of the second preferred embodiment. The data collected from the scanning process is preferably transferred with a universal to serial bus ("USB") to the computer 501 and/or central processor 503. The transfer can be done with wireless protocols or over a local area network ("LAN") connection. The user can calibrate the preferred 3D scanner 1200 with the same process and a checkboard that provides calibration for the lasers 1209, the cameras 1301 and processing capabilities of the 3D scanner 1200. The user can also check the lasers 1209, the motor 1250 that is preferably installed to or under the first endplate 1203, and the cameras 1301 part by part to diagnose the system of the 3D scanner 1200. Different motors or driving mechanisms can be used based on the precision and required speed to drive the movement of the tube 1205 along the rail 1202.

Referring to FIGS. 4, 5, 13 and 14, in the software of the second preferred 3D scanner 1200, the raw data of the cameras 1301, which preferably includes videos and/or pictures, is preferably processed in an image processing, or raw data step 404. The 2D images from the cameras 1301 are converted to 3D coordinates and the point cloud of the object. Following the initial scan, the central server or processor 503 and/or computer 501 analyzes the collected data to determine potential missing or underdeveloped areas of the object. The constructed file is preferably converted to a 3D mesh from point cloud in the point cloud step 406, the mesh is further processed in a mesh post-processing step 406-1 and the 3D mesh is finalized in a 3D digital file output step 407 so that the mesh can be exported in the desired format to the user. This 3D object file is used to input the mass customization software algorithms to design the fully automated or semi-automated brace, cast, and/or splint with the user specific parameters.

In the second preferred embodiment, the tube 1205 is preferably constructed of a lightweight structural material that is able to take on the size and shape of the tube 1205, withstand the normal operating conditions of the tube 1205 and perform the preferred functions of the tube 1205, as is described herein, such as a polymeric, metallic or other related material. The laser holders 1206 and camera mount 1302 are preferably constructed of a similar material to the tube 1205 and are mounted inside the tube 1205 but may alternatively be integrally formed or molded with the tube 1205. The laser holders 1206 and camera mount 1302 are preferably constructed of frusta-circular structural elements that mount to the inside of the tube 1205 and support the cameras 1301 and lasers 1209 within the tube 1205, respectively. The laser holders 1206 and camera mount 1302 include ends adjacent to the rail 1201 in the mounted configuration to facilitate connection to the rail 1201 and movement of the tube 1205 relative to the rail 1202.

The second preferred 3D scanner 1200 operates with the central processor 503, which is configured to receive data collected from the lasers 1209 and the cameras 1301 to construct the 3D model and define the cast, splint, brace or other support device. The central processor 503 preferably includes an algorithm that reconstructs an orthopedic cast, splint, or brace automatically based on a prescribed size, application, features such as deformities, ulcers, sores, wounds, or related features automatically or manually, as is described above. The algorithm preferably includes a classification algorithm configured to identify and predict a pre-fabricated cast, splint, or orthosis for the object, wherein the object is comprised of a body part of a patient. The algorithm also preferably includes a regressive algorithm configured to project database 3D models to 2D outlines in different planes. The preferred regressive algorithm is configured to adapt and scale 2D slices with the 2D images to generate the 3D model by slices with minimum error to the object. The algorithm also preferably includes mass customization in 3D scanned files to cluster into similar sizes.

In the second preferred embodiment, the central processor 503 includes a computer 501 and a processor 503 that are utilized to manipulate the data collected from the laser 1209 and the camera 1301 to develop or create the 3D model of the object.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present description.

We claim:

1. A scanner system for developing a 3D model of a body part of a patient, the scanner system comprising:

a capturing device configured to move around and capture images of the body part, the capturing device associated with a smart device configured to move around the body part to capture the images of a surface of the body part, the smart device including a graphical user interface configured to process images captured by the capturing device;

a central processor configured to receive the images of the body part from the capturing device and convert the images into a three-dimensional digital file of the body part, the central processor includes an algorithm that automatically reconstructs a model of an orthosis based on the three-dimensional digital file, the model of the orthosis designed as an appropriate type and size for an injury of the body part; and a three-dimensional printer configured to receive the model of the orthosis from the central processor and print an orthosis based on the model of the orthosis.

2. The scanner system of claim 1, wherein the algorithm is configured to engrave the model of the orthosis with a texture and a shape, the algorithm configured to locate an electric pad and a medical transducer in the model of the orthosis based on one of predicted features and user selection.

3. The scanner system of claim 1, wherein the algorithm is configured to insert markers into the model of the orthosis for one of injuries, medical records and prescribed notes with decision-making and natural language processing to customize the model of the orthosis in size, shape, engravement, pattern, length, and markers.

4. The scanner system of claim 1, wherein the algorithm includes a classification or machine learning algorithm configured to identify and predict one of pre-fabricated orthopedic casts, splints and braces for the body part, a size of the one of pre-fabricated cases splints and braces based on the images of the body part, organic mesh library, cad design library, and machine learning techniques.

5. The scanner system of claim 1, wherein the algorithm includes mass customization in the three dimensional digital file of the body part to cluster into similar sizes.

6. The scanner system of claim 1, wherein the capturing device is comprised of one of a smartphone and a tablet.

7. The scanner system of claim 1, wherein the images are comprised of at least one of two-dimensional and three-dimensional images of the body part.

8. The scanner system of claim 1, wherein the orthosis is comprised of one of an orthopedic brace, an orthopedic cast and an orthopedic splint.

9. The scanner system of claim 1, wherein the algorithm is comprised of a learning algorithm configured to detect and classify input object features of the body part including wounds, ulcer, deformities, sores and anomalies.

10. The scanner system of claim 1, wherein the smart device is comprised of one of a smartphone and a tablet, the augmented reality configured to facilitate visualization of a corrected position of the body part and permits adjustment of a position of the body part.

11. The scanner system of claim 1, wherein the graphical user interface includes augmented reality configured to guide the smart device around the body part to capture the images.

12. The scanner system of claim 1, wherein the capturing device is comprised of a laser, the laser configured to emit laser beams onto the body part and the scanner system configured to capture reflections of the emitted laser beams.

13. The scanner system of claim 1, wherein the capturing device is comprised of a smartphone having a graphical user interface in the form of a mobile application installed on the smartphone.

14. The scanner system of claim 13, wherein the mobile application is configured to guide a user in moving the smartphone around the body part to capture the images and to provide real-time feedback to the user indicating adequacy of the captured images for generating the three-dimensional digital file.

15. The scanner system of claim 1, wherein the central processor comprises a cloud-based server remote from the capturing device, the cloud-based server configured to receive the images from the capturing device over a network connection, automatically reconstruct the three-dimensional digital file from the received images, and transmit the model of the orthosis to the three-dimensional printer.

16. The scanner system of claim 1, wherein the algorithm is configured to reconstruct the three-dimensional digital file using photogrammetry techniques applied to a plurality of two-dimensional images of the body part captured by moving the capturing device around the body part.

17. The scanner system of claim 1, wherein the algorithm is configured to engrave a lattice pattern into the model of the orthosis to provide ventilation and breathability to the orthosis when printed by the three-dimensional printer.

18. The scanner system of claim 1, wherein the algorithm is configured to incorporate a locking mechanism into the model of the orthosis.

19. The scanner system of claim 18, wherein the locking mechanism is configured to permit the three-dimensional printer to print the orthosis in a configuration that is selectively convertible between a locked cast configuration and a removable splint configuration.

20. The scanner system of claim 1, wherein the graphical user interface is configured to receive physician-specified positioning instructions and limb positioning parameters for incorporation into the model of the orthosis, the central processor configured to adjust the model of the orthosis based on the physician-specified positioning instructions.

21. The scanner system of claim 1, wherein the algorithm is configured to select and optimize three-dimensional printing parameters for printing the orthosis from a biocompatible, waterproof polymeric material, the printing parameters including at least one of infill percentage, shell size, raster angle, and print orientation.

22. The scanner system of claim 1, wherein the graphical user interface is configured to display a visualization of the three-dimensional digital file overlaid with one or more of surgical incision locations, post-surgical hardware locations, and scarring locations on the body part.

23. The scanner system of claim 22, wherein the algorithm is configured to customize the model of the orthosis to accommodate the one or more overlaid locations.

24. The scanner system of claim 1, wherein the graphical user interface is further configured to receive manually-entered body measurements of the body part from a user, to integrate the manually-entered body measurements with the three-dimensional digital file to compensate for movement of the body part during image capture and to adjust the model of the orthosis at predetermined fit points.

25. The scanner system of claim 1, wherein the capturing device, the central processor, and the three-dimensional printer are configured to operate as a turnkey point-of-care fabrication system located at a single clinical facility.

26. The scanner system of claim 25, wherein the system is configured to produce the orthosis at the clinical facility within a few hours from the time of capturing the images of the body part.

27. The scanner system of claim 1, wherein the algorithm is configured to engrave one or more of a clinic identifier, a logo, and a patient identifier into a surface of the model of the orthosis.

28. The scanner system of claim 1, wherein the algorithm is configured to generate a plurality of different models of orthoses from a single three-dimensional digital file of the body part, the plurality of different models comprising at least a first model for a full cast configuration and a second model for a splint configuration.

29. The scanner system of claim 1, further comprising:

a slicing module integrated with the central processor, the slicing module configured to convert the model of the orthosis into printer-executable instructions compatible with the three-dimensional printer, the printer-executable instructions generated automatically by the algorithm without requiring manual intervention by a user.

30. A method of processing and making a custom orthosis for a patient's injured limb with a capturing device, a central processor in communication with the capturing device and a three-dimensional printer in communication with the central processor, the method comprising:

collecting measured distances of the injured limb;

receiving the measured distances at the central processor;

capturing images of the injured limb with the capturing device by moving the capturing device around the injured limb, augmented reality of the central processor utilized to guide a user in capturing the images;

receiving the images at the central processor from the capturing device;

developing a digital file of the injured limb based on the images;

comparing the measured distances to the digital file of the injured limb;

developing a three-dimensional model of an orthosis based on the digital file;

transmitting the three-dimensional model of the orthosis to the three-dimensional printer;

printing an orthosis based on the three-dimensional model to fit the injured limb;

analyzing the images of the injured limb to determine potential underdeveloped areas of the injured limb, the capturing device comprises a camera and a backup camera; and actuating the backup camera to collect image data when the central processor detects the underdeveloped areas.

31. The method of claim 30, wherein the central processor includes a graphical user interface associated with a smart device, the smart device moving around the injured limb to capture the images of the injured limb.

32. The method of claim 31, wherein the graphical user interface processes the captured images and transmits the three-dimensional model to the three-dimensional printer.

33. The method of claim 30, wherein the central processor includes an algorithm, the algorithm utilized to optimize three-dimensional-printing parameters of a three-dimensional printer that prints the orthosis, including one of fill percent, lattice shape, shell size, speed, raster angle and orientation.

34. The method of claim 30, further comprising:

inserting markers into the three-dimensional model of the orthosis to identify injuries of the injured limb.

35. The method of claim 30, further comprising:

detecting one of a wound, sore, deformity and anomaly of the injured limb based on the captured images of the injured limb.

36. The method of claim 30, wherein the digital file is comprised of one of a three-dimensional digital file and a two-dimensional digital file.

37. The method of claim 30, wherein capturing the images of the injured limb with the capturing device includes capturing laser beams reflected from the injured limb.

38. A method of processing and making a custom orthosis for a patient's injured limb with a capturing device, a central processor in communication with the capturing device and a three-dimensional printer in communication with the central processor, the method comprising:

collecting measured distances of the injured limb;

receiving the measured distances at the central processor;

capturing images of the injured limb with the capturing device by moving the capturing device around the injured limb, augmented reality of the central processor utilized to guide a user in capturing the images;

receiving the images at the central processor from the capturing device;

developing a digital file of the injured limb based on the images, the digital file is comprised of a three-dimensional digital file of the injured limb;

comparing the measured distances to the digital file of the injured limb;

developing a three-dimensional model of an orthosis based on the digital file;

transmitting the three-dimensional model of the orthosis to the three-dimensional printer; and printing an orthosis based on the three-dimensional model to fit the injured limb, wherein the central processor includes an algorithm, the algorithm configured for visualizing a corrected position of the injured limb and to adjust the three-dimensional digital file to the corrected position.

39. The method of claim 38, further comprising:

converting the three-dimensional digital file to a three-dimensional mesh.

40. The method of claim 38, wherein the three-dimensional digital file of the injured limb is developed in combination with a machine learning module of the central processor, the machine learning module trained by a dataset of three-dimensional digital files of body parts.

41. A scanner system for capturing a three-dimensional model of an injured limb, the scanner system comprising:

a laser configured to provide a stripe of light to illuminate the injured limb;

a camera configured to capture images of the injured limb;

a tube mounted to a rail, the tube configured to move generally along a travel axis of the rail, the tube including a first tube end and a second tube end, the first and second tube ends being open, the laser and the camera mounted inside the tube between the first tube end and the second tube end, the first tube end including a first continuous ring and the second tube end including a second continuous ring, a channel extending through the tube between the first and second continuous rings and positioned adjacent the rail in an assembled configuration; and a central processor configured to receive data collected from the laser and the camera, the central processor configured to analyze the images of the injured limb to determine potential underdeveloped areas of the injured limb, the camera comprises a camera and a backup camera, the central processor configured to actuate the backup camera to collect image data of the injured limb when the central processor detects the potential underdeveloped areas; and an actuation mechanism configured to move the tube along the rail generally along the travel axis.

42. The scanner system of claim 41, wherein the laser is comprised of an array of lasers.

43. The scanner of claim 41, wherein the camera is comprised of an array of cameras.

44. The scanner of claim 41, wherein the images are comprised of one of two-dimensional images and three-dimensional images.

* * * * *